(12) United States Patent
Wilf et al.

(10) Patent No.: US 9,727,787 B2
(45) Date of Patent: Aug. 8, 2017

(54) SYSTEM AND METHOD FOR DERIVING ACCURATE BODY SIZE MEASURES FROM A SEQUENCE OF 2D IMAGES

(71) Applicant: SIZER TECHNOLOGIES LTD, Hertzelia (IL)

(72) Inventors: Itzhak Wilf, Savyon (IL); Orlee Hadas Tal, Tel Aviv (IL); Adam Spiro, Tel Aviv (IL); Eyal Gluska, Tel Aviv (IL); Mordechay Gust, Haniel (IL)

(73) Assignee: SIZER TECHNOLOGIES LTD, Hertzelia (IL)

( * ) Notice: Subject to any disclaimer, the term of this patent is extended or adjusted under 35 U.S.C. 154(b) by 0 days.

(21) Appl. No.: 14/616,247

(22) Filed: Feb. 6, 2015

(65) Prior Publication Data
US 2015/0154453 A1    Jun. 4, 2015

Related U.S. Application Data

(63) Continuation-in-part of application No. PCT/IL2013/050743, filed on Sep. 3, 2013.
(Continued)

(51) Int. Cl.
G06K 9/00 (2006.01)
G06K 9/46 (2006.01)
(Continued)

(52) U.S. Cl.
CPC ........ *G06K 9/00711* (2013.01); *A61B 5/1079* (2013.01); *A61B 5/486* (2013.01);
(Continued)

(58) Field of Classification Search
None
See application file for complete search history.

(56) References Cited

U.S. PATENT DOCUMENTS 8,068,676 B2 *  11/2011  Zhang ................ G06K 9/00362
                                             382/111
2002/0126295 A1  9/2002  Dudkiewicz et al.
(Continued)

FOREIGN PATENT DOCUMENTS

| | | |
|---|---|---|
| GB | 2351426 A | 12/2000 |
| WO | 2006071006 A1 | 7/2006 |
| WO | 2011156474 A2 | 12/2011 |

OTHER PUBLICATIONS

International Search Report dated Dec. 22, 2013 for PCT/IL2013/050743.
(Continued)

*Primary Examiner* — Tahmina Ansari
(74) *Attorney, Agent, or Firm* — Kinney & Lange, P.A.

(57) ABSTRACT

A method for deriving accurate body size measures of a user from a sequence of 2D images includes: a) automatically guiding the user through a sequence of body poses and motions; b) scanning the body of said user by obtaining a sequence of raw 2D images of said user as captured by at least one camera during said guided sequence of poses and motions; c) analyzing the behavior of said user to ensure that the user follows the provided instructions; d) extracting and encoding 2D shape data descriptors from said sequence of images by using a 2D shape analyzer (2DSA); and e) integrating said 2D shape descriptors and data representing the user's position, pose and rotation into a 3D shape model.

18 Claims, 22 Drawing Sheets

Related U.S. Application Data

(60) Provisional application No. 61/696,816, filed on Sep. 5, 2012.

(51) Int. Cl.
*G06K 9/48* (2006.01)
*G06T 17/00* (2006.01)
*A61B 5/107* (2006.01)
*A61B 5/00* (2006.01)
*G06T 7/564* (2017.01)
*G06T 7/62* (2017.01)
*A41H 1/02* (2006.01)

(52) U.S. Cl.
CPC ..... *G06K 9/00208* (2013.01); *G06K 9/00369* (2013.01); *G06K 9/46* (2013.01); *G06K 9/48* (2013.01); *G06T 7/564* (2017.01); *G06T 7/62* (2017.01); *G06T 17/00* (2013.01); *A41H 1/02* (2013.01); *G06K 2009/4666* (2013.01); *G06T 2207/10024* (2013.01); *G06T 2207/30196* (2013.01)

(56) References Cited

U.S. PATENT DOCUMENTS

| | | | |
|---|---|---|---|
| 2009/0116698 A1* | 5/2009 | Zhang | G06K 9/00362 382/111 |
| 2010/0111370 A1* | 5/2010 | Black | G06K 9/00369 382/111 |
| 2015/0154453 A1* | 6/2015 | Wilf | G06K 9/00711 382/103 |

OTHER PUBLICATIONS

Supplementary Partial European Search Report dated Sep. 23, 2016, for corresponding European Application No. 138535345.

Alexander Weiss et al.: "Home 3D body scans from noisy image and range data", Computer Vision (ICCV), 2011 IEEE International Conference on IEEE, Nov. 6, 2011, pp. 1951-1958.

Adrian Hilton et al.: "Whole-body modelling of people from multiview images to populate virtual worlds", Visual Computer, vol. 16, No. 7, Nov. 1, 2000, pp. 411-436.

* cited by examiner

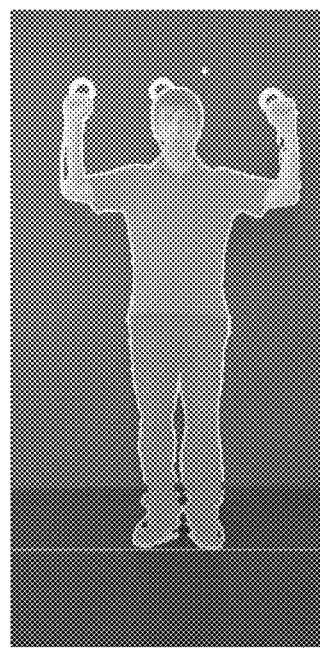
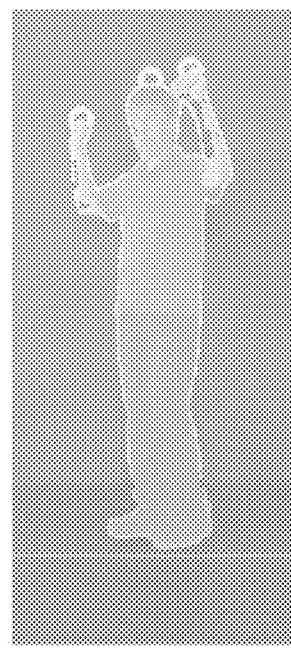
Fig. 5A          Fig. 5B
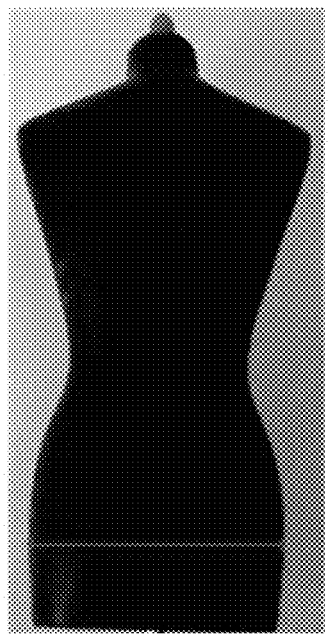
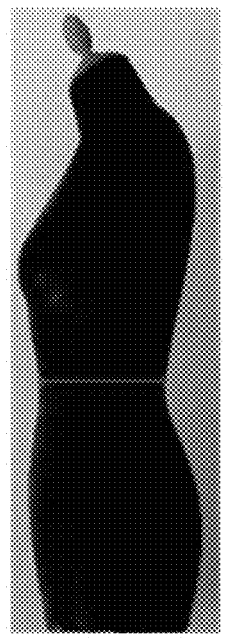
Fig. 6A          Fig. 6B

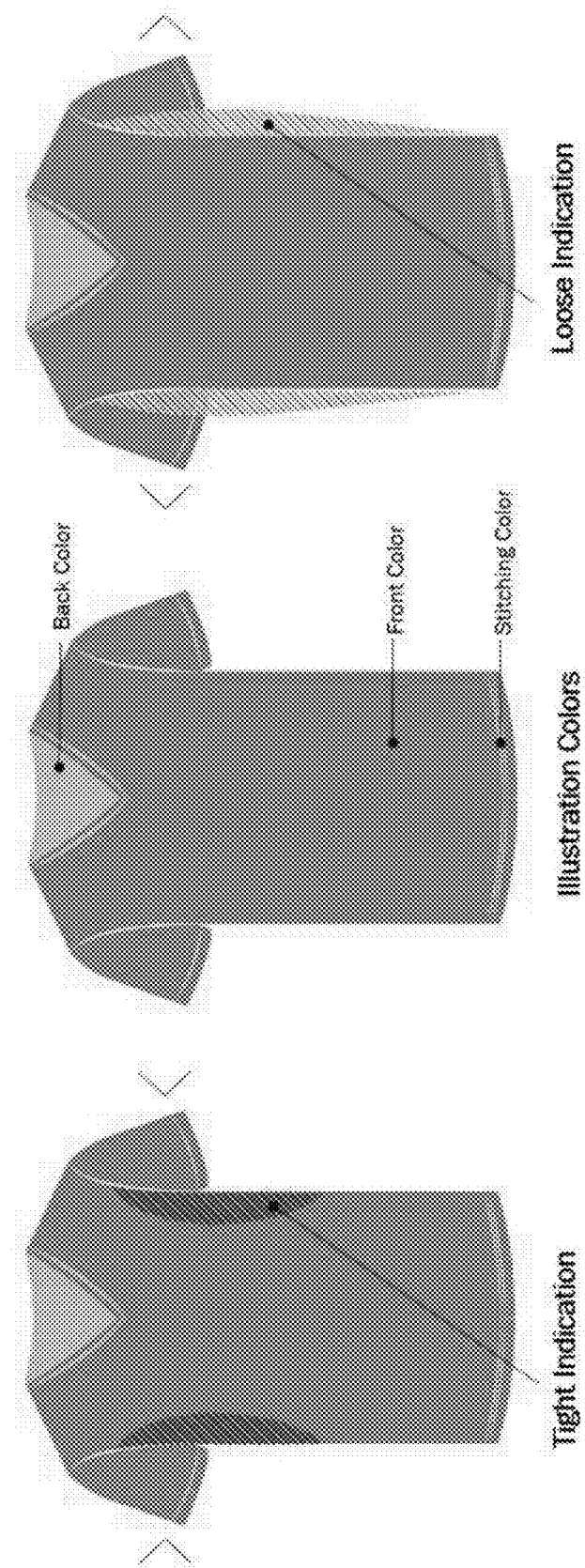

SYSTEM AND METHOD FOR DERIVING ACCURATE BODY SIZE MEASURES FROM A SEQUENCE OF 2D IMAGES

FIELD OF THE INVENTION

The present invention relates to the field of body scanning and garment selection systems. More particularly, the invention relates to a system and method for body scanning to enhance the experience of garment shopping, through automated size recommendation and augmented reality visualization.

BACKGROUND OF THE INVENTION

Full body scanners—laser scanners/array of depth cameras (such as the Kinect® by Microsoft Corporation) can be used to capture three dimensional (3D) points on the body's surface, which can be used to represent the body shape as in point form (e.g. cloud of points), surface form (mesh of triangles), or other models. Such models can be analyzed to extract the required measurements. For example, the waist location can be computed from body proportions and the cross section at waist height can be used to extract a list of points or a contour representing the circumference at that point. The perimeter is than computed from said 3D list of points/contour.

The cost and complexity of building a full body scanner are prohibitive for mass deployment in stores and/or consumer in-home usage. Therefore, several prior art techniques describe how to extract specific body measurements from a single two dimensional (2D) image (usually a front view) and optionally a few other additional views of controlled pose (e.g. a side view). Considering for example the waist circumference, it is clear that one or two views cannot provided enough information to compute the exact circumference without further assumptions or approximation—for example an elliptical cross section of the body at the waist area. Clearly such approximations fail to provide exact measures when real subjects are involved.

Other prior art methods are more flexible with regard to environment, or user pose, but rely on parameterized and statistical shape models in order to solve for the shape of a specific user. For example, US 2010/0111370 discloses a system and method of estimating the body shape of an individual from input data such as images or range maps. The disclosed method captures the statistical variability across a human population with a smaller number of parameters (e.g., fewer than 100). To represent a wide variety of human shapes with a low-dimensional model, statistical learning is used to model the variability of body shape across a population (or sub-population). It is clear however, that quite often, relying on statistical models may result in significant errors for any single user, as compared with the requirements for garment fittings or for monitoring patients undergoing treatment. In such applications, accuracy requirements are 98% or better.

Furthermore, to be commercially viable, the measurement process will be performed by the inexperienced user at his/her apartment and without additional human guidance/observation. The process must be short and exhibit a high rate of success—in the first attempt.

It is an object of the present invention to provide a system which is capable of automatically guiding the user through a sequence of body poses and motions that include at least partial rotation.

It is another object of the present invention to provide a system which is capable of ensuring that the user correctly follows guiding instructions provided by the system.

It is yet another embodiment of the present invention to provide a system which is capable of providing instructions and ensuring steps that relates to the choice of measurement site/scene, camera positions, measurement garment color and tightness, and other environmental parameters that may aid to improve the quality of the measurements.

Other objects and advantages of the invention will become apparent as the description proceeds.

SUMMARY OF THE INVENTION

Embodiments of the present invention relate to a method for deriving accurate body size measures of a user from a sequence of 2D images, comprising: a) automatically guiding the user through a sequence of body poses and motions, that include at least partial rotation, by providing a set of instructions, wherein said automatic guiding is based on real-time visual monitoring of the user and the surrounding scene; b) scanning the body of said user by obtaining a sequence of raw 2D images of said user as captured by at least one camera during said guided sequence of poses and motions; c) analyzing the behavior of said user to ensure that the user follows the provided instructions, by using a user behavior analyzer (UBA) module that tracks the position, pose/rotation and posture of said user before and during the guided sequence of poses and motions and matching them against posture/motion models stored in a Posture/Motion database; d) extracting and encoding 2D shape data descriptors from said sequence of images by using a 2D shape analyzer (2DSA); and d) integrating said 2D shape descriptors and data representing the user's position, pose and rotation into a 3D shape model, wherein said integration includes assigning rotation values to said sequence of images, wherein said values are either absolute values with respect to a full frontal position, or relative with respect to a reference image in said sequence.

According to an embodiment of the invention, integrating the 2D shape descriptors and data representing the user's position, pose and rotation into a 3D shape model includes deriving torso circumference values by intersecting convex areas computed by back projecting silhouette edge points according to user position and rotation associated with each silhouette image. For example, the torso circumference values can be measured at one or more of: waist, hips and chest positions, and the respective position can be selected using at least one of: silhouette image analysis, extremum selection from a set of circumference values and anthropometric ratios.

According to an embodiment of the invention, the method further comprises providing a user feedback and guidance module (UFGM) for interacting with the user during the scanning, including providing initial and further user guidance/assistance during the scanning.

According to an embodiment of the invention, the initial user guidance/assistance includes at least one of: positioning the user with respect to the sensor field of view, positioning the user with respect to the background and background objects, advising the user to select a different location for the measurement process, advising the user to modify certain environmental elements in the scene, or advising the user one how to modify the device position and orientation.

According to an embodiment of the invention, the further user guidance/assistance includes at least one of: presenting a small audio-visual guide prior to the scanning process, before and during every step in the scanning sequence, presenting audio-visual instructions describing the posture/motion to be performed controlling the duration/pace of the posture motion by audible cues such as music/sound bites, monitoring the execution of the required postures and issuing corrective instructions, performing initial quality assessment of measurement metadata derived from current/prior postures/motions and guiding the user to repeat one or more postures/motions if so required.

According to an embodiment of the invention, presenting audio-visual instructions, or issuing corrective instructions includes presenting a virtual guiding figure, positioned and scaled according to the user location.

According to an embodiment of the invention, the real-time visual monitoring of the user includes analyzing the scene/background as captured by the camera(s) by measuring dynamic and static image contents in said captured scene, thereby enabling to qualify the scene as a body measurement site, to suggest changes to the scene and to suggest optimal user positioning in the scene in form of the set of instructions.

According to an embodiment of the invention, the method further comprises extracting and encoding visual non-shape descriptors of the user including face appearance descriptors of the user by a user appearance analyzer (UAA), wherein said non-shape descriptors represents attributes related to the appearance of said user and may include skin tone, hair color and style.

According to an embodiment of the invention, the method further comprises estimating the distance from the user's image height and the user's physical height, as a single size value that either can be manually provided to the system via an input device, or the distance/location can be automatically extracted from the sequence of images.

According to an embodiment of the invention, the method further comprises guiding the user to rotate at least a quarter of a circle and measuring the body rotation angle relative to a full frontal pose by tracking individual body parts that include at least left hand, right hand or top of head.

According to an embodiment of the invention, the method further comprises detecting a body silhouette width evolution of the user as a key to body rotation, by tracking the evolution width sequence of binary images and estimating the rotation angles in-between using interpolation technique.

According to an embodiment of the invention, analyzing the behavior of the user further comprises verifying that the user's image does not exceed the field of view of the camera.

According to an embodiment of the invention, the method further comprises providing garment recommendation to the user by using a recommendation engine.

In another aspect, embodiments of the present invention relate to a system for deriving accurate body size measures of a user from a sequence of 2D images, comprising: a) a camera for scanning the body of said user by capturing a sequence of raw 2D images of said user; b) a user behavior analyzer (UBA) for analyzing the behavior of said user and to ensure that said user follows the provided instruction, by tracking the position, pose/rotation and posture of said user before and during the body scanning and matching them against stored against posture/motion models stored in a Posture/Motion database; c) a 2D shape analyzer (2DSA) for extracting and encoding 2D shape data descriptors from said sequence of images; and d) a processing unit programmed for receiving said 2D shape descriptors as well as the user's position, pose and rotation data and integrating them into a 3D shape model, wherein said integration includes assigning rotation values to said sequence of images, wherein said values are either absolute values with respect to a full frontal position or relative, with respect to a reference image in said sequence.

According to an embodiment of the invention, the system further comprises a user feedback and guidance module for interacting with the user during the scanning, including providing initial and further user guidance/assistance during the scanning.

According to an embodiment of the invention, the system further comprises a user appearance analyzer (UAA) for extracting and encoding visual non-shape descriptors of the user.

According to an embodiment of the invention, the system further comprises a user shape and appearance database for storing 3D size measurements of the user body together with the user appearance data.

According to an embodiment of the invention, the system further comprises a garment database for storing garments related data.

According to an embodiment of the invention, the system further comprises garment recommendation engine (GRE) for providing garment recommendation to the user.

In another aspect, an embodiment of the present invention is a non-transitory computer-readable medium comprising instructions which when executed by at least one processor causes the processor to perform the method of the present invention for deriving accurate body size measures of a user from a sequence of 2D images.

BRIEF DESCRIPTION OF THE DRAWINGS

In the drawings:

FIGS. 5A and 5B depict hands detection and tracking as body rotation detection cue, according to an embodiment of the present invention;

FIGS. 6A and 6B schematically illustrate body silhouette width evolution as key to body rotation;

FIG. 19A-19C is a schematic drawing depicting the way the garment may fit the body, according to an embodiment of the invention.

DETAILED DESCRIPTION OF THE INVENTION

The present invention relates to a method that employs a sequence of 2D images captured through specific body movements monitored and guided in real-time to compute multiple linear and circumference body size measures (i.e., a body scanner). Such measures can serve as basis to automated size recommendation for more efficient in-store or in-home shopping experience. These size measures can be further used to select and/or modify an avatar or other visual representation that best describes the user's body shape for augmented reality visualization of how the selected garment would fit or look on the user's body. Additionally, the scanning method can be used to obtain a cloud of points or other dense 3D representation that serve as a detailed body shape model. The required measurements are derived from that model. The 3D representation can be converted to a surface model (like triangle mesh) that can be used by a rendering engine of an augmented reality application.

In concept, the body scanner can be used anywhere, e.g., in a retail store or shopping mall or inside the user's home. As the most common use case for the body scanner, is an individual measuring himself or herself in the convenience of his or her home, in an unassisted manner. Hence the embodiments according to the present invention are most suitable for that case, and will work similarly or better in other use cases—such as a measurement booth with or without guidance by a sales representative. The user stands on the floor in a state of undress, usually in a tight-fitting body suit, wherein the goal is to obtain accurate and complete body measurements. Typically, no try-on garment is used as a basis for finding fit incongruities or to obtain an individual's feedback. The user's body scan measurements are provided to a computer program for analysis. The program compares the user's measurements to the properties/specifications of the selected garment such as its dimensions in certain key locations, fabric elasticity, garment fit & tolerance. The system's analysis may result in a recommendation for a garment and the specific size that would fit the user perfectly.

In the following detailed description, references are made to the accompanying drawings that form a part hereof, and in which are shown by way of illustration specific embodiments or examples. These embodiments may be combined, other embodiments may be utilized, and structural changes may be made without departing from the spirit or scope of the present invention. The following detailed description is therefore not to be taken in a limiting sense and the scope of the present invention is defined by the appended claims and their equivalents. One skilled in the art will readily recognize from the following description that alternative embodiments of the structures and methods illustrated herein may be employed without departing from the principles of the invention described herein.

Figure 1:
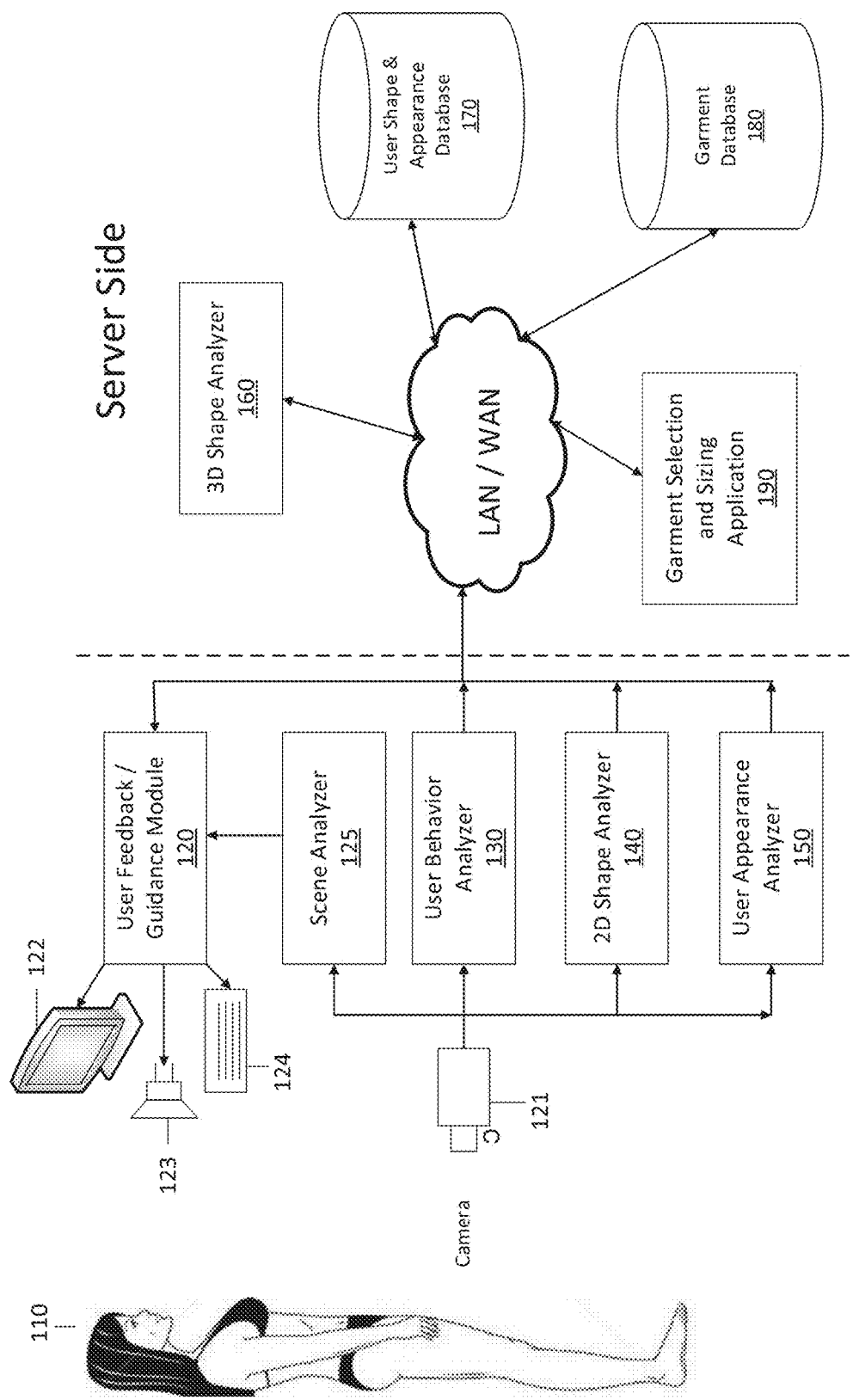
FIG. 1 schematically illustrates a system for body scanning and garment selection, according to an embodiment of the invention.

Referring now to the drawings, in which aspects of the present invention and an exemplary computing operating environment will be described. FIG. 1 and the following discussions are intended to provide a brief, general description of a suitable computing environment in which the invention may be implemented. While the invention will be described in the general context of program modules that execute in conjunction with a virtual fitting room application program that runs on an operating system on a personal computer, those skilled in the art will recognize that the invention may also be implemented in combination with other program modules.

Generally, program modules include routines, programs, components, data structures, and other types of structures that perform particular image processing tasks. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network (e.g., a user side and a server side). In a distributed computing environment, program modules may be located in both local and remote memory storage devices.

In the following description, a 2D image is defined as a dense array of point measurements, where the array is indexed in 2 dimensions (usually denoted by (x, y)). Point measurements may be any subset of the following attribute: I, R, G, B, and Z (where "I" stands for Intensity, "R", "G", and "B" for Red, Green and Blue, "Z" for depth). One or more attributes may be replaced by equivalent representations such as Hue-Saturation-Value (HSV), etc., as an alternative color space, stereoscopic disparity values, time of flights, etc.

The embodiments shall be generally described for (R, G, and B) arrays which are widely available from current image sensors and cameras, but can be generalized with required modifications to other attributes. According to one such modification, the sensor provides a depth map and the background subtraction technique is applied to Z values, thus facilitating the detection of foreground objects, even when their colors are similar to those of the background, FIG. 1 describes a system 100 for deriving accurate body size measures from a sequence of 2D images, according to an embodiment of the present invention. In general, system 100 is used for body scanning and garment selection. System 100 comprises a User Feedback and Guidance Module (UFGM) 120, camera 121, a Scene Analyzer 125, a User Behavior Analyzer (UBA) 130, a 2D Shape Analyzer (2DSA) 140, a User Appearance Analyzer (UAA) 150, a 3D Shape Analyzer (3DSA) 160, a garment and size selection application 190 (herein a virtual fitting room application) and a garment database 180.

A user 110 is positioned in front of the camera 121, with a display 122 and a speaker 123 driven by the UFGM 120 to provide initial and further user guidance/assistance during the scanning process of the user's body. An input device, such as a keyboard 124, a touch screen or voice command/audio module, may serve to start the scanning process, enter user ID, except user consent for measurement, etc.

Camera 121 is connected to Scene Analyzer 125 which analyzes the scene/background as captured by the Camera, by applying a measurement process to the captured scene/background that measures the scene dynamic content as well its static image content, for qualifying the scene as a body measurement site, for suggesting changes to the scene and for suggesting user positioning in the scene to maximize the ease and accuracy of the measurement process. Said suggestions are communicated to the user through the User Feedback/Guidance Module 120.

Camera 121 is further connected to UBA 130, which tracks the position, pose/rotation and posture of the user 110 before and during the scanning process, verifying that the user's image does not exceed the camera's Field Of View (FOV) and that the user is following the instructions provided by the UFGM 120. Such instructions may include: "Enter the Scanning Area", "Raise Your Hands", "Turn Around", etc.

Camera 121 is further connected to the 2DSA 140, which extracts and encodes 2D shape data from each of a sequence of images captured by the camera 121.

Camera 121 is further connected to the UAA 150, which extracts and encodes visual non-shape descriptors specific to the user. Such descriptors may include skin tone, hair color and style and optionally face appearance descriptors. These descriptors can be used by the virtual fitting room application 190 to enhance the visual appearance of the avatar to resemble the user—for example having a skin-tone similar to the user, having a face similar to the user, etc.

The visual non-shape descriptors may be further used to generate clothing recommendations based on one or more of these descriptors. For example a recommended garment color and/or texture/pattern may enhance the skin tone, the hair color, and the eyes.

Each element of system 100 can be implemented by a separate module such as a USB webcam, LCD display, connected speakers, a keyboard, a personal computer, etc. However, with introduction of highly capable consumer electronic devices, certain embodiments of the present invention can be based on such devices. In a specific example all elements of system 100 can be implemented by a user's computer based device such as a laptop computer, a tablet computer such as the iPad by Apple Inc. or even a smartphone such as the Galaxy by Samsung.

According to another embodiment of the present invention, some modules of system 100 can be implemented in a remote server, such as the 3DSA 160, and the garment database 180. The 3DSA 160 receives the 2D shape descriptors as well as the user position, pose and rotation data, integrating them into a 3D shape model and/or extracting 3D size measurements to be stored together with the user appearance data in a User Shape and Appearance Database 170. When a previously scanned user logs into the system 100 (e.g., via an interface of the virtual fitting room application 190) his stored body size characteristics are used to filter/search the garment database 180 and recommend garments and their specific sizes that will be a good fit for the user. In another case which is better aligned with current shopping experience, in response to a user selection of a garment on a web shop, the user may receive a size recommendation as well as a schematic drawing depicting the way the garment may fit the body (an example for such a schematic drawing is presented in FIGS. 19A-19C). FIG. 19A shows a schematic representation of tight indications in form of black diagonal lines at both side of a T-shirt. FIG. 19B shows a schematic representation of color illustrations on top of the T-shirt, such as back color, front color and stitching color. FIG. 19C shows a schematic representation of loose indications in form of white diagonal lines at both side of a T-shirt.

Garment database 180 includes data that digitally represent garments such as shirts, trousers, dresses, etc. and their attributes, such as size, length, width, color, etc., as commonly defined by the clothing industry. For example, in order to add garments to the database 180, the system 100 may further comprise a garment detection module (not shown). In order to provide the correct scale and perspective for the detected garment and optionally to eliminate or reduce distortions that may occur due to the camera view angle and the plane on which the garment is located, known in the art distortion correction techniques should be used, such as using an object with known dimensions as a reference object (e.g., a Compact Disk) or a calibration pattern such as a chessboard pattern.

According to an embodiment of the invention, the 3D shape information is further used to build an avatar that best describes the user's body shape for augmented reality visualization of how the selected garment would fit or look on the user's body. For a more powerful presentation, user appearance information as obtained from the UAA 150 is embedded into the avatar in the form of skin/hair color and also a similar face, provided that the user opted for his/her face to be captured during the scanning process. With the growing computing power of such user's computer based devices, the 3DSA 160 can be included on such a device, further reducing computational resources and bandwidth requirements on the server side.

Figure 2A:
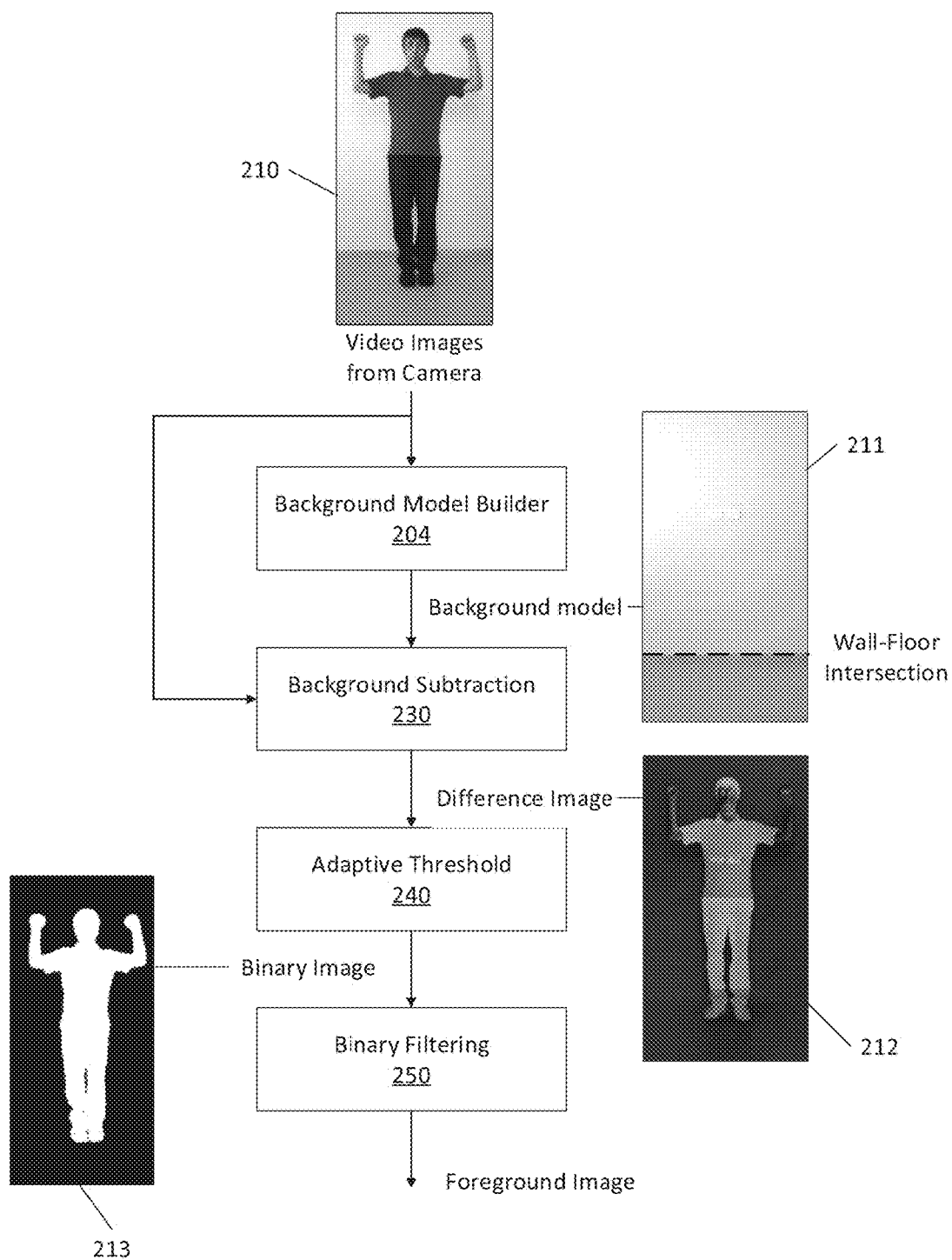
FIG. 2A is a flow chart generally illustrating a method for foreground detection as known in prior art.

FIG. 2A describes a method for foreground detection that is commonly used to detect changes in image sequences, as known in the prior art. As the scanning process will be performed indoors and the camera 121 (FIG. 1) will be static during the process, a background subtraction technique is appropriate. A background modeling process (step 220) constructs a background model as a running average of video images that do not contain foreground objects—before the user enters the scene or by inhibiting averaging in those areas where the frame-to-frame difference is high, thus signaling user presence or motion. An exemplary image of a background model is indicated by numeral 211. The background model is generated and maintained by the Scene Analyzer 125 (FIG. 1).

The Scene Analyzer 125, User Behavior Analyzer 130 and UFGM 120 are further designed to identify and propose corrective actions for several common user-scene cases. These cases will be described hereinafter for the specific approach of background subtraction, but similar scenarios and related guidance are applicable for different user segmentation methods.

Figure 2B:
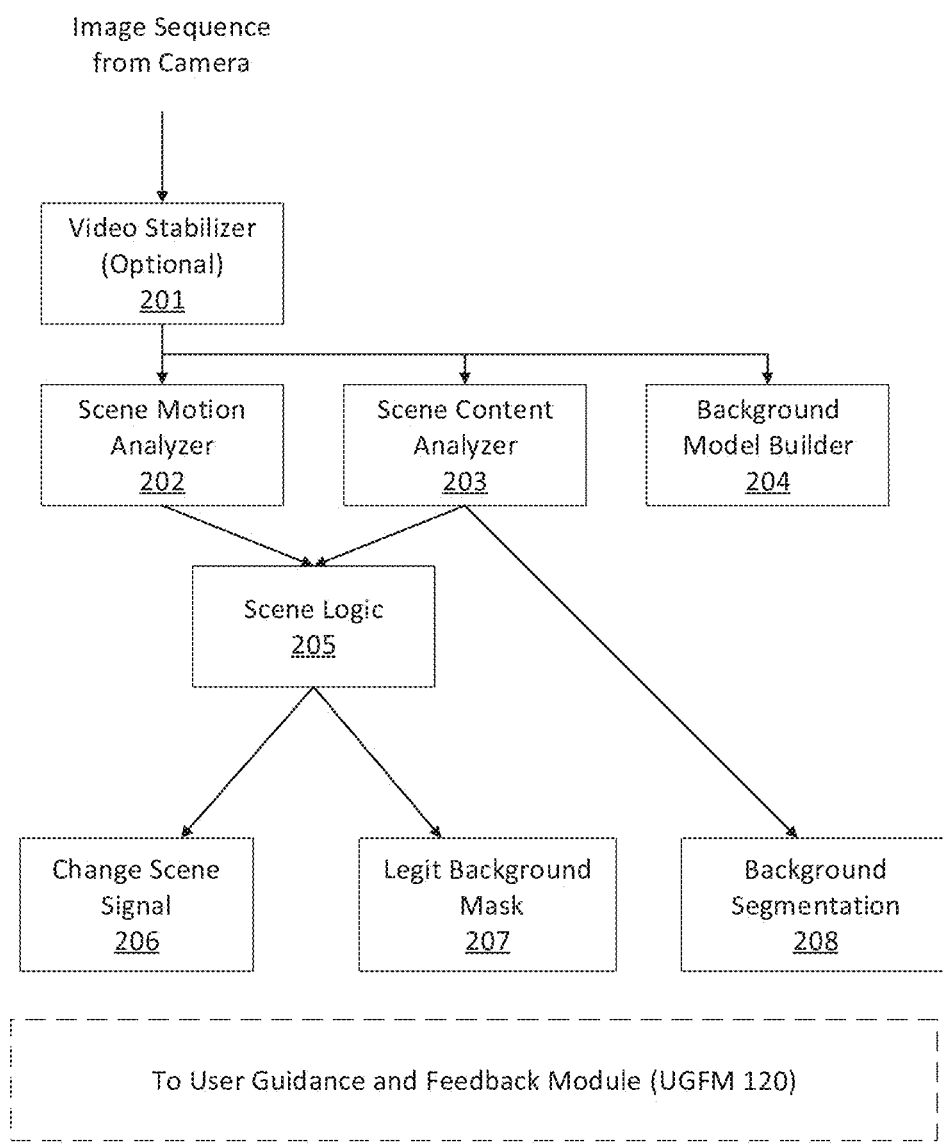
FIG. 2B schematically illustrates the Scene Analyzer, according to an embodiment of the invention.

FIG. 2B is schematically illustrates a possible embodiment of the Scene Analyzer 125 which analyzes the background in the absence of the user, and if necessary signals the UGFM 120 that instructs the user to change the current measurement location or to do some changes in the measurement site in order to avoid possible environmental disturbances. A video stabilizer 201 allows to analyze the scene while the user is holding a mobile device adapted for self-capturing and measurement the user's body. In a common scenario the user is looking for a suitable measurement site. When the mobile device is placed on a stable object, such as on a chair, the sensors of the mobile device are capable of detecting that the mobile device is in a stable position, thereby avoiding the need to perform video image stabilization by video stabilizer 201.

With zero/compensated device motion, Scene Motion Analyzer 202 measures the temporal variation from the scene image sequence on a pixel-by-pixel basis. In certain cases, only limited portions of the background image may be dynamic, and the background motion analysis shall designate these portions as "Illegal" in the Legit Background Mask 207 according to scene logic 205.

Scene Content Analyzer module 203 further analyzes one or more frames of the background, measuring its edge/texture content. According to a related method background content analysis shall analyze the color distribution of the background alerting on skin-like color that may interfere with user foreground detection.

Both modules 202 and 203 may use scene logic 205, which is adapted to decide when to apply the Legit Background Mask 207 to the background motion analysis and/or when to generate "change scene" signals 206 to UGFM 120 in order to instructs the user to change the current measurement location or to do some changes in the measurement site in order to avoid possible environmental disturbances.

According to an embodiment, module 203 includes a Background Segmentation Module 208, which divides the background images into meaningful parts, in the context of the planned guided user body measurement. For example, a wall-floor intersection line of a background wall that appears in the scene, as indicated by the dotted line in image 211 in FIG. 2A, is identified and helps characterize the scene for the planned user guided postures and motions.

In certain cases, only a limited portion of the background image may include problematic edge/texture/color elements, and the background content analysis shall designate that portion for a User Positioning Stage described herein after with respect to module 303 in FIG. 3A.

A Background Model Builder 204 is also incorporated into the embodiment of Scene Analyzer 125. The Background Model 204 is a part of the Foreground Detection scheme depicted in FIG. 2A. During scene analysis a statistical model of the background is constructed. The model may be as simple as a single scene image captured when the device is placed in its final position and orientation. Typically multiple scene images are used to build the background model, by collecting multiple samples for each scene picture element (pixel) and then computing a statistical model for each such element that may be the mean/robust mean and also include the temporal variance/robust variance in order to set the threshold as indicated by numeral 240 (adaptive threshold) in FIG. 2A.

Figure 3A:
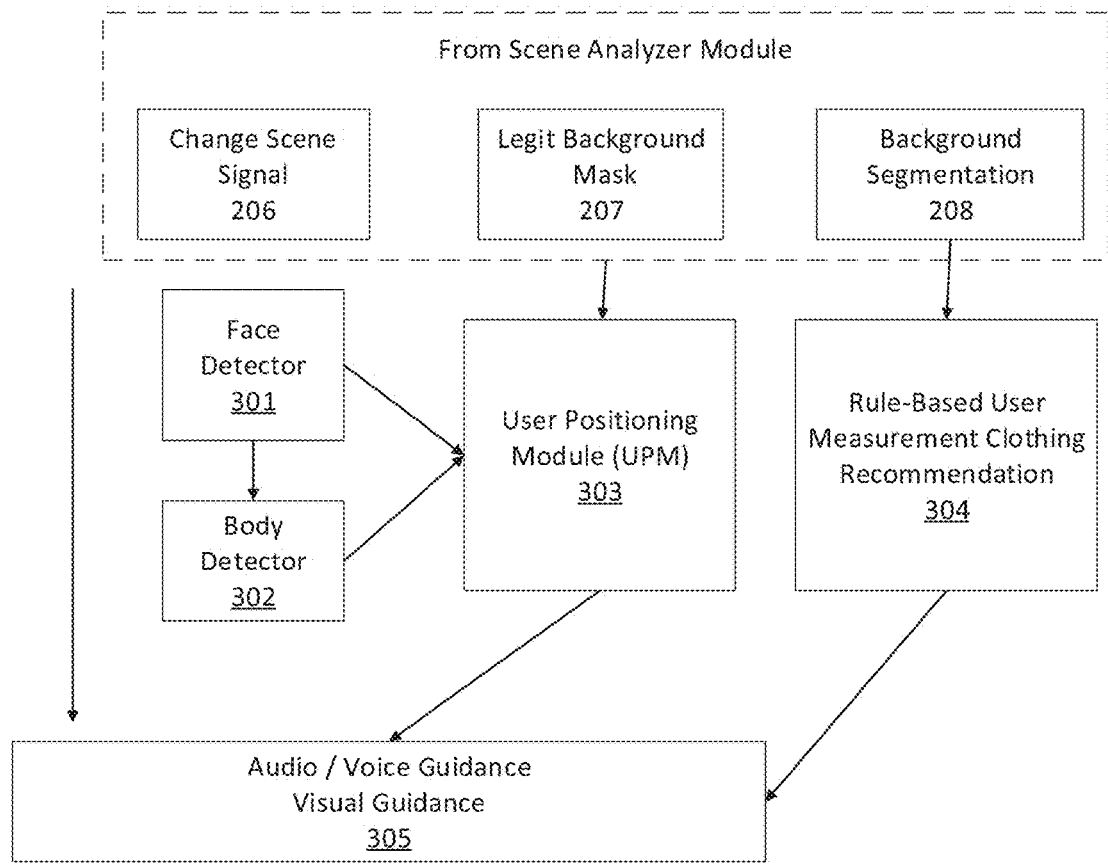
FIG. 3A schematically illustrates the User Feedback/Guidance Module (UFGM), according to an embodiment of the invention.

Referring now to FIG. 3A, according to one embodiment, the UGFM 120 may include a rule-based user clothing recommendation module 304 that may advise the user how to better be detected with respect to the appearance of the background at measurement scene, for example, to wear white socks to facilitate feet detection, if the floor is dark or highly patterned.

Before starting the scan, a User Positioning Module (UPM) 303 of the UGFM 120 may position the user in the device field of view (FOV), ensuring that the entire user figure is visible. Using known image detection methods such as face detection 301 and human body detection 302, such verification can be done without a background model or background subtraction step.

In the case that limited portions of the scene are dynamic/contain problematic elements, such that the user can be safely positioned in the "safe" scene areas with enough margins to allow the required postures and motions to be performed, UPM 303 may position the user accordingly.

In a case that UPM 303 cannot position the user properly in the device FOV, e.g., due to the scene dynamics/image content as described above, the UGFM 120 may instruct the user to perform certain modification to scene elements (e.g., shut down a TV screen, remove certain elements from the scene if possible) or move the device and repeat the process elsewhere.

In another case, the UPM 303 determined that the user image cannot fit entirely into the device FOV, for example when a back wall is too close to the device. The user than will be advised to move the device farther back, to position it in a tilted position on the floor or select another location.

To reduce measurement time, improve user experience and increase accuracy, the UGFM 120 may use several embodiments of Man-Machine Interaction.

According to one embodiment the UGFM 120 provides voice/audio guidance in terms of voice commands/instructions. The UGFM 120 sound options may include pre-recorded rhythms selected to control user motion (rotation in particular) and guide it into a constant angular velocity.

Figure 18A:
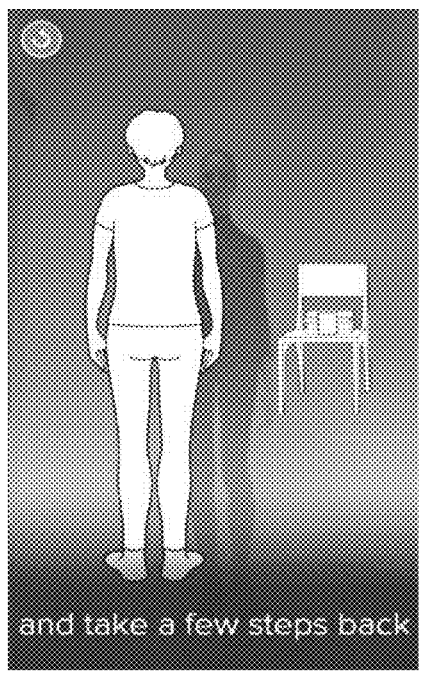
FIG. 18A-18D show exemplary screen layout of a real-time view of the captured scene that are combined with a virtual guide presenting the posture/motion to be performed by subject user.
Figure 18B:
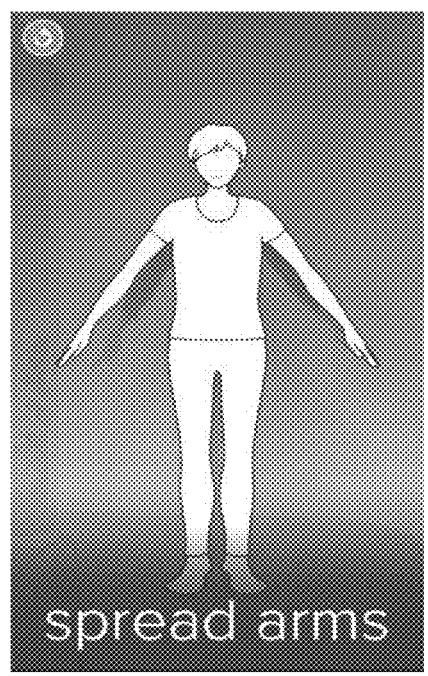
Figure 18C:
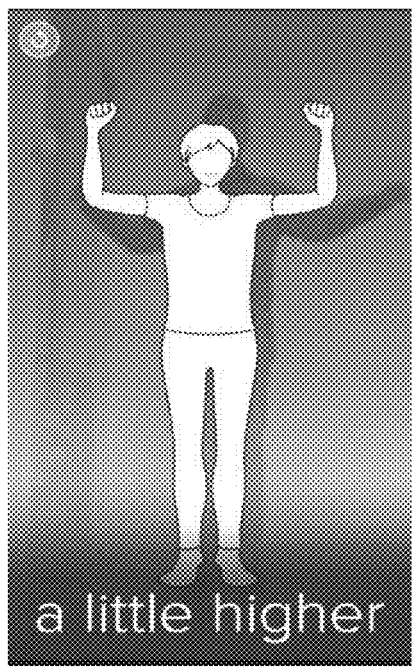

According to one embodiment, the UGFM 120 combines a real-time view of the captured scene, with a virtual guide presenting the posture/motion to be performed, as shown in FIG. 18A. To enhance the accuracy of such performance, the virtual guide is optionally aligned with the user image as shown in FIG. 18B. As the image position and scale of the user are computed by the User Behavior Analyzer 130 (FIG. 1), the virtual guide is positioned and scaled accordingly to focus the attention of the user on a single location, and allow the user to perceive easily the postures/motions or related adjustments to be performed by him/her.

Referring now back to FIG. 2A, once the scene, the user positioning and clothing are confirmed, according to one embodiment, the user may be asked to exit the scene, to facilitate background learning by Background Model Builder 204. Once the background model is stable (as indicated by numeral 211), the user is guided to move back into the scene. Then for each newly captured video frame, a background subtraction module (step 230) computes the pixel-by-pixel absolute difference between the video frame (as indicated by numeral 210) and the background model image 211. The difference image (as indicated by numeral 212) is then processed by an adaptive threshold (step 240) which sets its threshold globally or locally (per image location) just above the noise and illumination changes level to obtain a binary image (an exemplary binary image is indicated by numeral 213). A binary filtering step 250 may use known techniques such as connected component filtering or morphological filtering to eliminate small noise regions and small holes inside the object.

Figure 3B:
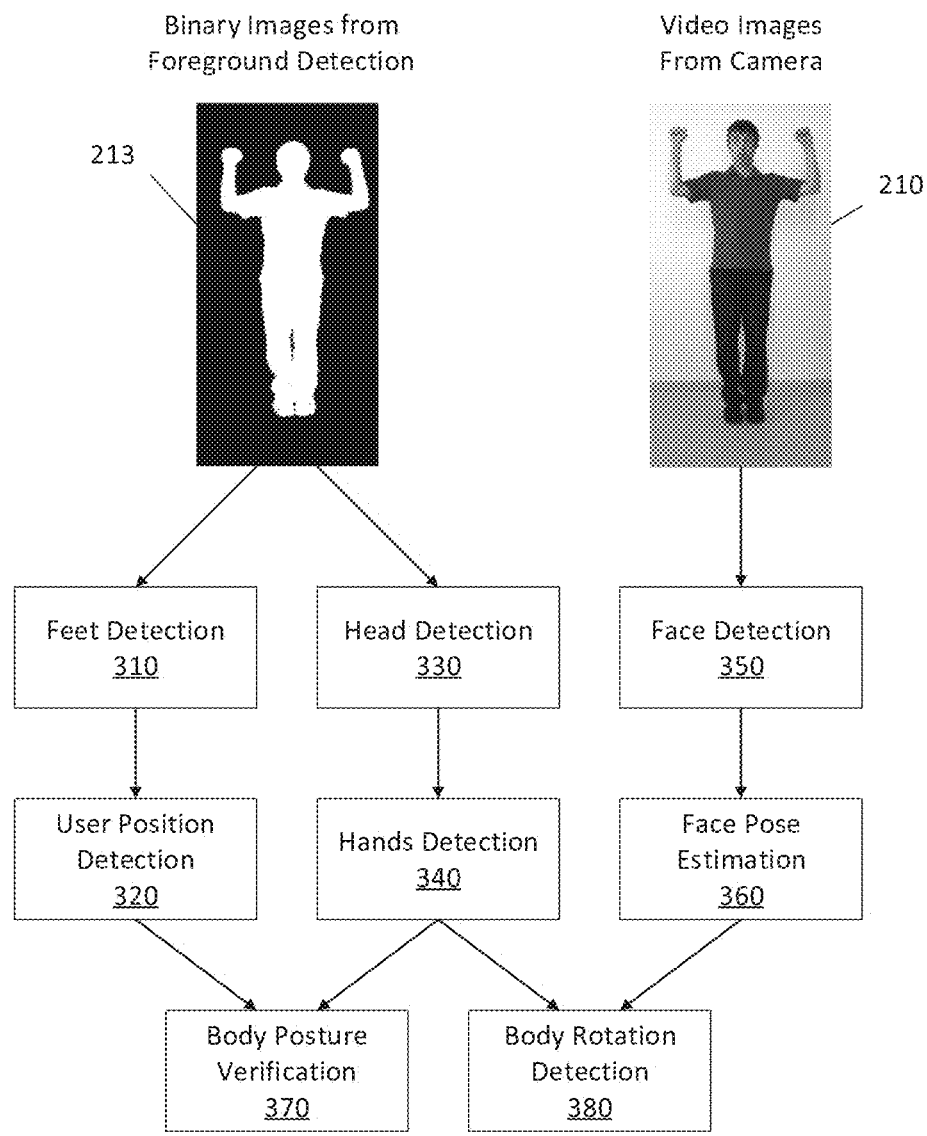
FIG. 3B describes a method for analyzing user behavior as required for the scanning process, according to an embodiment of the invention.

FIG. 3B schematically illustrates, in a flowchart form, the process of analyzing user behavior by UBA 130 as part of the scanning process, according to an embodiment of the present invention. For the purpose of obtaining a user 3D shape data, user behavior information may include:

User position on a ground plane;

User pose or rotation with respect to the ground plane; and

Verification of the required posture as instructed by the UFGM 120.

During the following description, it is assumed that the scanning process is directed at the user's torso for the purpose of measuring such circumferences as waist, hip and chest and/or for obtaining a 3D cloud of points describing the torso area. In a specific embodiment, torso scanning is performed with the user assuming a "Cactus" position so that the torso area is un-occluded throughout the scanning process—as outlined by image 210 in FIGS. 2A and 3B.

The User Guidance and Feedback Module (UGFM) 120 closely monitors the output of the User Behavior Analysis module, as described herein below with respect to FIG. 3C, and continuously guides the user through audio-visual messages on completion of measurement steps, next postures/motions to be performed and corrective actions/steps.

User behavior is analyzed based on the binary body silhouette as obtained from the foreground detection process (as indicated by image 213 in FIG. 2A) and the raw video images from the camera 121 (FIG. 1).

According to an embodiment of the present invention, one key attribute of user behavior analysis is the estimation of the location of the human subject. In one embodiment, the human subject is requested to maneuver in a designated area throughout the scanning process, optionally using on-floor markings can be used to guide the user through the scanning process. Alternatively, the system can estimate the distance from the subject's image height and the subject's physical height, as a single size value that may be manually input to the system (e.g., via the keyboard 124 shown in FIG. 1). However, for better accuracy, fully automatic operation and a less cooperative subject, the system extracts the distance/location from the 2D image sequence.

Figure 4:
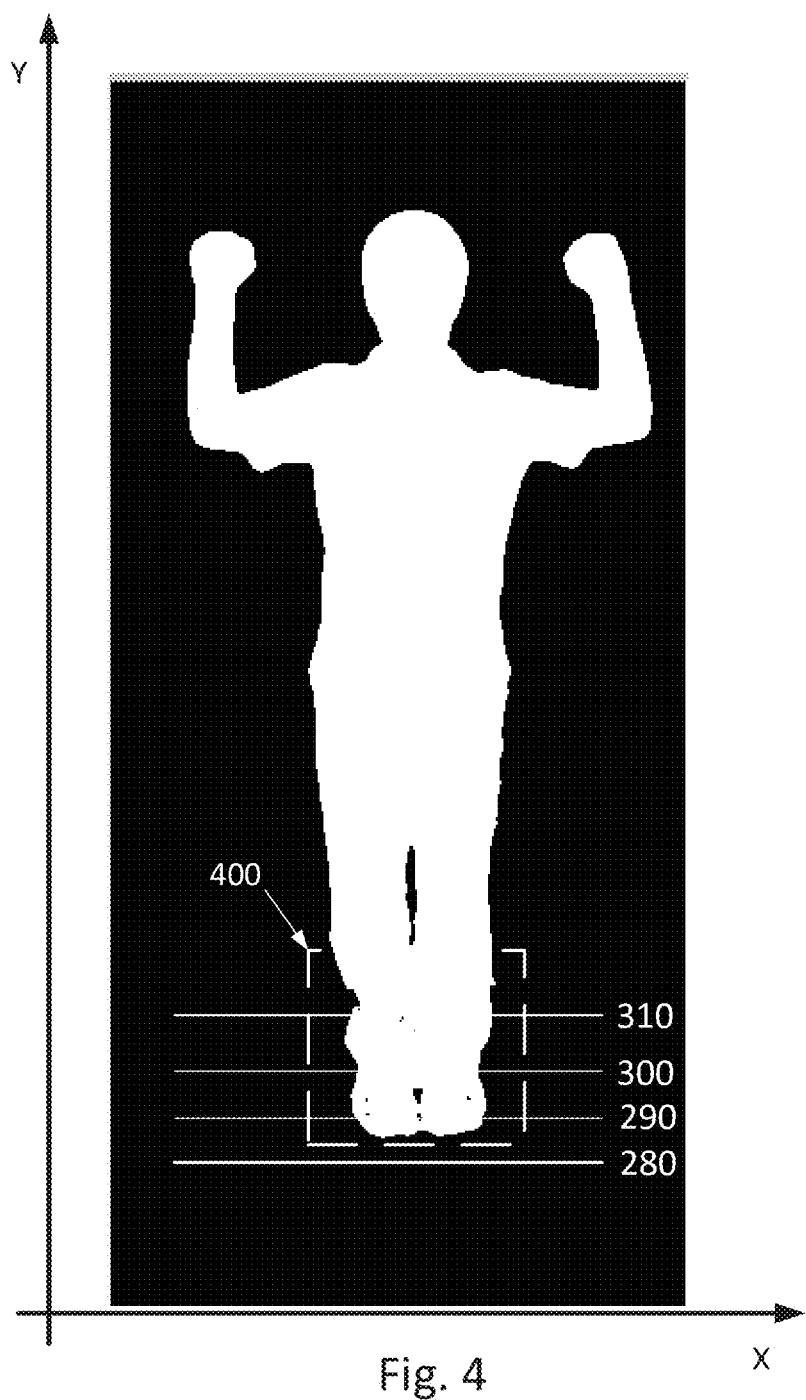
FIG. 4 illustrates the extraction of user distance from feet image position detection.

Analyzing user behavior by UBA 130 may involve the following steps:

Feet detection (step 310), searches for the bottom row of the binary silhouette. Based on camera calibration that takes place in the beginning of the scanning processes, each image row (y) coordinate depicting the floor surface can be converted to a distance from the camera. For example, FIG. 4 illustrates the extraction of user distance from feet image position detection in further details. Calibrated distance lines 280, 290, 300 and 310 are shown as horizontal lines with distance values. Vertical feet position between lines can be interpolated. To assign exact distance value to the center of rotation, the system converts the bottom of feet distance to body center distance using an average value for feet size and (optionally) the body rotation angle.

Once the bottom image position is detected, a computation window (as indicated by the dashed line 400) is constructed around the feet and the x-axis center-of gravity is converted to on-floor horizontal position (from camera calibration). This completes the user position detection (step 320).

To avoid instability of object segmentation at the feet area to affect the position accuracy, both y bottom coordinate and x center-of-gravity are temporally filtered, for example, by using a 5-frame averaging filter or other suitable averaging filter.

The user distance can be estimated in a similar manner from the top of head location by detecting and tracking the head as described in the present invention. Both these methods for distance tracking—from feet detection only or from head detection only, require knowing the camera height from the floor and it tilt. While this readily available in a fixed camera installation such as in a fitting room, we may desire supporting in-home application when measuring the camera height and controlling/measuring its tilt may be annoying for a one-time user. In such a case, one may combine the embodiments according to the present invention in order to track both head and feet location, thus deriving the user's distance at each measurement frame without requiring the camera height/tilt values.

If the user is too close to the camera, which may result in clipping of the user silhouette and/or increased perspective distortion, the user feedback UFGM 120 will provide a warning to the user. Similarly, if the user is too close to a wall behind, which may result in difficulty to turn, another warning will be delivered. The UFGM 120 (FIG. 1) includes multiple of scene content and user behavior analysis algorithms as known in prior art, for detecting common problems in scene and camera setup and user behavior such as: lighting is too low or too bright, background is too busy, dynamic background such as TV monitor or computer screen in the camera field of view, moving shades, moving cast lights, camera is tilted, etc.

Based on the binary silhouette, head detection module (step 330) can find the user's head as the top of the binary shape, near the horizontal (x) center of gravity. Further verification/fine location of head position can be based on an omega-shaped head-shoulder detector or other known human detection and tracking techniques such as face detection.

Once the head and the feet are detected, a general scale is available for the entire shape and may serve as initial guess for the location of certain body parts, using anthropometric length/height ratios. Hands detection module (step 340) starts searching for the arms from the estimated shoulder positions, then moves up (for this specific posture) to detect the hands as the endpoints of the arms' shape. Alternatively, the binary shape (e.g., see the exemplary image 213) can be thinned to a 1-pixel wide skeleton/medial axis transform image as known in mathematical morphology, where the hand tips cab be detected as 1-connected pixels at the end of the arm skeleton tracked from center body location.

Figure 18D:
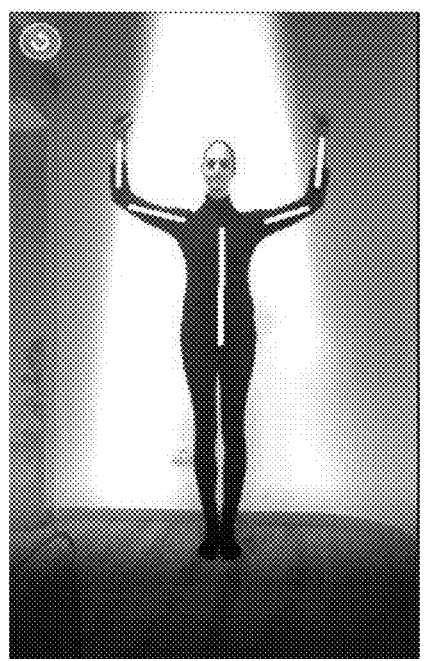

For the specific case of morphological skeleton-based shape analysis, the main elongated parts of the human figure are further represented by straight line segments as shown in FIG. 18D. It is then possible to measure the relative angles of arm and hands, verify the user posture and issue audible and visual commands for corrections if necessary. A common posture error might be lowering the elbows to below bust level, which may interfere in the correct measurement of bust circumference, as described below. If such an error is detected, the UGFM 120 may request the user to raise his/her elbows further, in a voice command, by displaying a virtual figure with the correct posture or displaying a short animation.

Having estimated the user position from the feet silhouette, the system goes on (step 370) to verify the body posture as described above and then to guide the user to rotate a full circle or at least 90 degreed rotation (the guidance can be done by UFGM 120). Image sequence continuity can be exploited in hand tracking. Once both hands are detected in a frontal position, they are tracked from frame to frame (e.g. using correlation search or other common Digital Image Correlation and Tracking (DIC/DDIT) methods that employ tracking and image registration techniques for accurate 2D and 3D measurements of changes in images). Alternatively, one may perform structural analysis as depicted in FIG. 18D and obtain hand-tip coordinates on a frame-by-frame based. When approaching 90° rotation, the hands projections merge with the head silhouette and one has to rely on prediction and interpolation to estimate the hands position and continue tracking when the hands can be detected again—as the user continues to rotate towards 180° position.

Figure 3C:
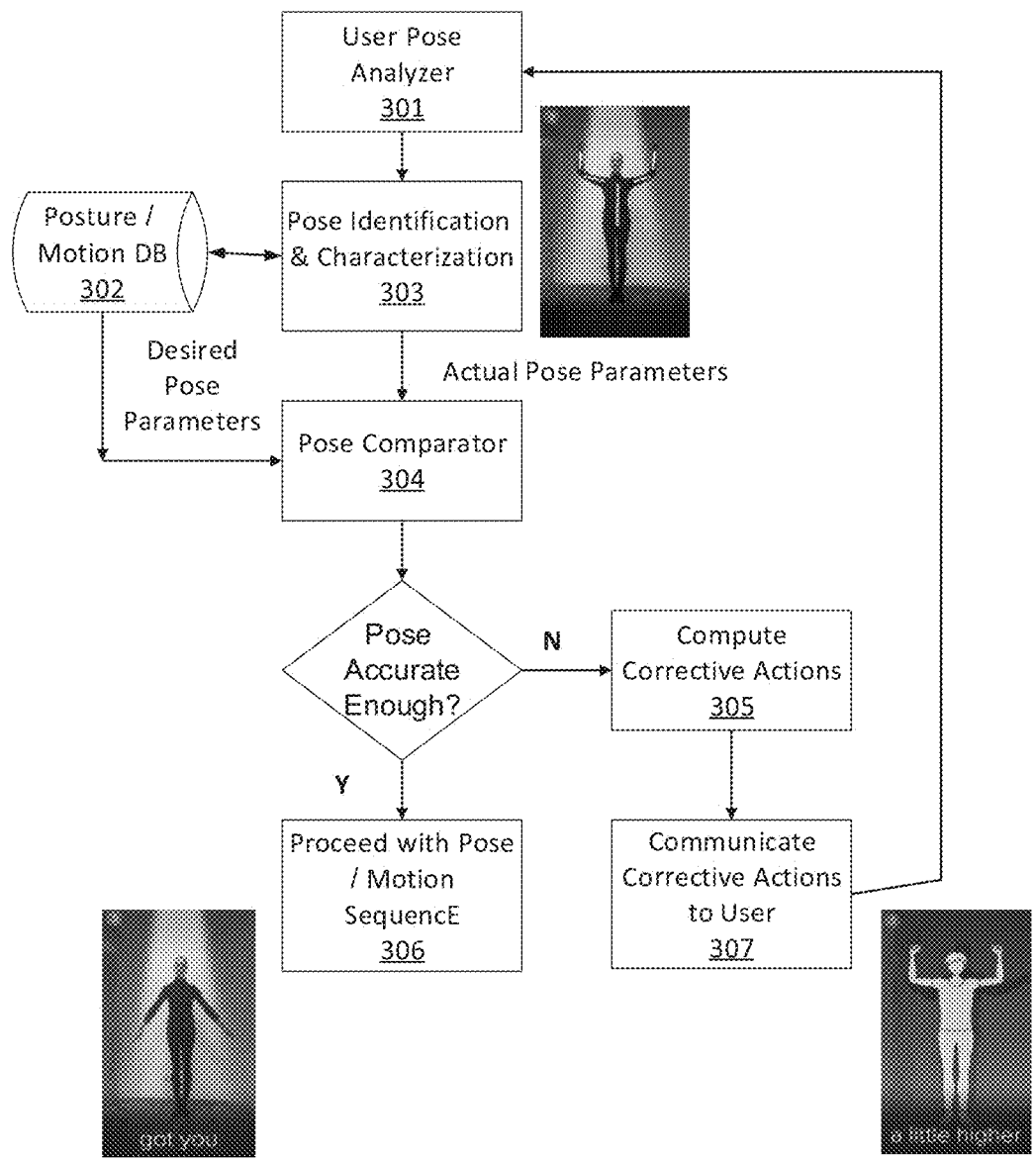
FIG. 3C depict the method of ensuring that the user follows the instructions provided by the UFGM, according to an embodiment of the invention.

FIG. 3C depict the method of ensuring that the user follows the instructions provided by UFGM 120, by using the UBA 130 module that tracks in real time the position, pose/rotation and posture of said user before and during the guided sequence of poses and motions. A User Pose Analyzer 301 analyzes the user pose/motion, as shown in FIGS. 18A-18D. The detected pose/body elements are matched against posture/motion models stored in a Posture/Motion database DB302 to identify the corresponding pose/motion from the guided sequence. For example, DB 302 may contain posture/motion models such as "Standing Hands Up", "Spread Legs", "Rotate Slowly to the Left", etc. Once the pose is identified, DB 302 outputs pre-stored Desired Pose Parameters such as angle between limbs. Given the identified pose and a Pose Analyzer Output, module 303 then generates the corresponding Actual Pose Parameters. In the specific example depicted herein, the user hands must be raised high enough before and during rotation, to ensure that the torso circumference at the chest line level is visible during rotation, thereby allowing to compute that circumference from the body silhouette as outlined below.

A Pose Comparator 304 compares the Desired Pose Parameters with the Actual Pose Parameters. If the difference is small or insignificant with the respect to the body size measured derived from that specific pose, a Positive User Feedback is generated and the guided sequence proceeds as planned. However, in the case that the Pose is not accurate enough—for example the user hands in FIG. 18D are raised too high, module 305 computes Corrective Actions and communicates them to the user via Module 307—which may include user voice commands, or graphics indications, guiding the user to lower or raise his/her hands.

In order to integrate 2D image shape data into 3D sizes/shape, it is required to assign rotation values (either absolute—with respect to a full frontal position or relative, with respect to a reference image in the sequence) to the sequence images.

FIGS. 5A and 5B depict hands detection and tracking as body rotation detection cue, wherein FIG. 5A depicts the body of user 110 in a first position, while FIG. 5B depicts the body of user 110 in another position that is rotated with respect to the first position of FIG. 5A. Numeral 510 indicate the user's head while numerals 511 and 512 indicate the user's hands. Assuming that the 3D distance between the hands 511 and 512 remains fixed during the short rotation, body rotation detection module (step 380) tracks the evolution of the image distance in order to provide rotation angle estimates. Other body rotation cues can be used, independently or combined in order to increase precision.

For example, one may track the visual content inside the body silhouette—such as garment patterns and skin texture. Applicable techniques include feature point detection and tracking [Carlo Tomasi and Takeo Kanade, "Detection and Tracking of Point Features", Carnegie Mellon University Technical Report CMU-CS-91-132, April 1991]. Body rotation can be estimated from computing an "optical flow" field of visual motion and fitting a motion model to the vector field [John L. Barron, David J. Fleet, and Steven Beauchemin (1994), "Performance of optical flow techniques", International Journal of Computer Vision (Springer)]. Such techniques can be augmented by face rotation tracking as described below.

Face detection module (step 350) focuses face search on the head detected by head detection module (step 330). A face detector such as the Viola-Jones face detector can be applied to the images in order to detect faces in a variety of frontal poses, and has been extended also to detect profile faces. The specific classifier providing the best score provides a sense of face pose. Accuracy is further increased by detecting multiple face landmarks and estimating pose from the relative positions and distance ratios.

FIGS. 6A and 6B schematically illustrate a body silhouette width evolution as key to body rotation, wherein FIG. 6A shows the body silhouette in a first position, while FIG. 6B shows the body silhouette in another position that is rotated with respect to the first position of FIG. 6A. For example, the image with narrowest waist dimension (min of min) may be assigned 90° and the one with the widest hip dimensions (max of max) may be assigned 0°. The system then tracks the evolution the width sequence and estimates the rotation angles in-between using interpolation, such as:

Linear interpolation—assuming constant angular velocity;

Width-based interpolation—assuming an elliptical cross section of the waist/hip;

Tracking the motion of visual details inside the body silhouette, using known optical flow techniques or feature point detection and tracking as described hereinabove, and solving for the rotation using an elliptical cross section model.

The aforementioned process of analyzing user behavior by UBA 130 describes the user behavior analysis on a frame-by-frame basis. Segmentation and analysis errors may result in noisy measurements and/or spurious values at isolated frames. All user behavior parameters can be smoothed in the temporal domain (over time) to provide robust estimates of said parameters. As one specific example, a median filter or other robust estimator as known in statistics can be applied to the sequence of body rotation angles in order to reduce random angular errors and filter out outliers.

Figure 7:
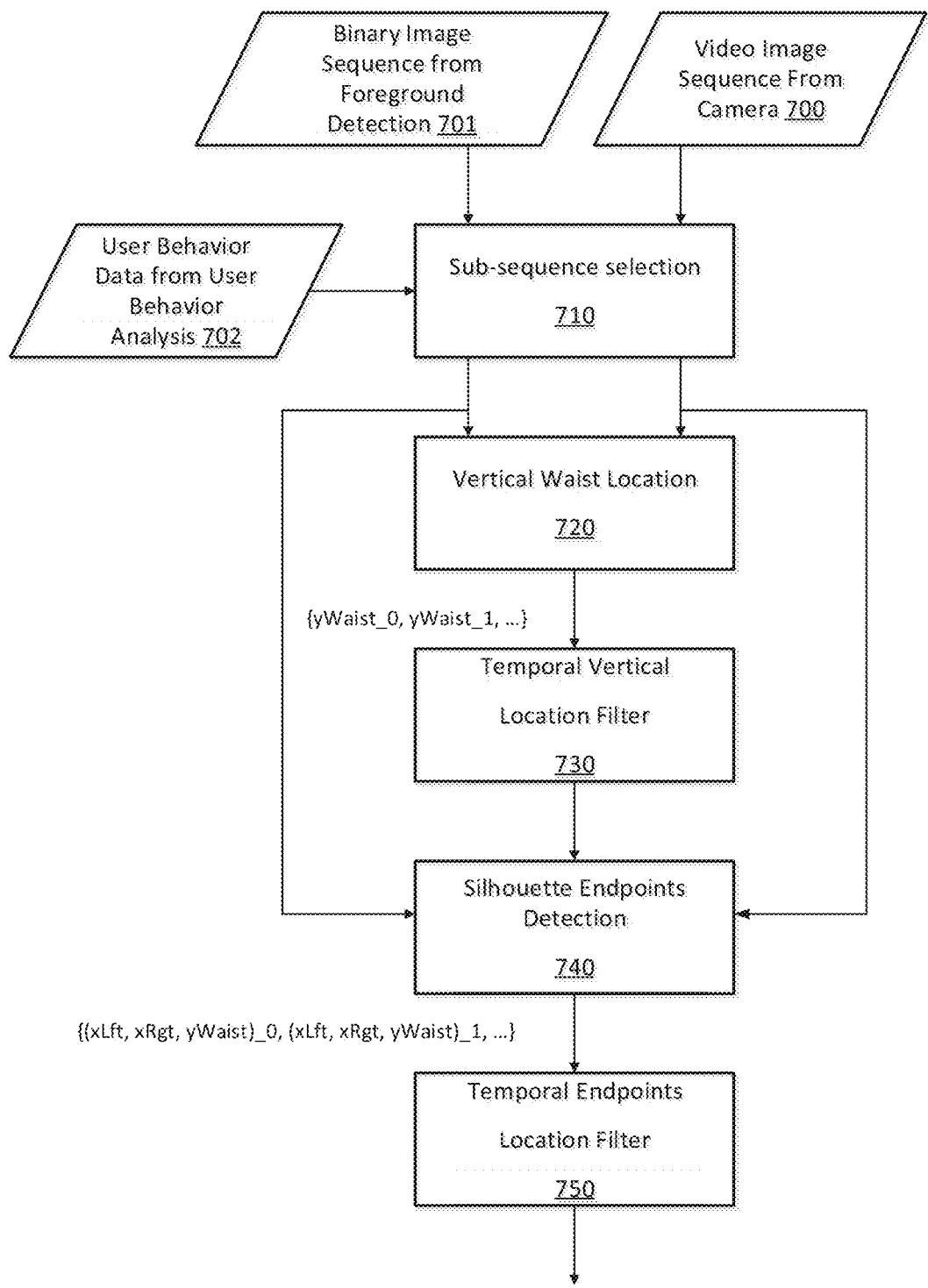
FIG. 7 describes 2D Shape Analyzer, according to an embodiment of the present invention.

FIG. 7 describes, in a flowchart form, the process of analyzing 2D shape by 2DSA 140, according to an embodiment of the present invention. For better clarity, we describe the 2D shape analysis in the context of a specific size measurement—the waist circumference.

According to an embodiment of the present invention, 2D shape analysis requires detecting the waist image location at multiple images of the rotation sequence and then measuring the edge or contour points of the waist at each such image.

According to FIG. 7, a sub-sequence selection module (step 710) employs user behavior data (step 702) from UBA 130 (as described hereinabove with respect to FIG. 3B) to select a sub-sequence of images from the video image sequence (step 700) and its foreground image counterpart (step 701) as obtained from the foreground detection module (as described hereinabove with respect to FIG. 2A). This allows to skip irrelevant images (for example when no user location data is available or when the user is not in the right posture), as well as to skip redundant images (when the user does not move or rotates very slowly).

Vertical waist location module (step 720) then detects the vertical image location of the waist for selected images of the sub-sequence, as described hereinafter with respects to the images shown in FIGS. 8A-8C.

Silhouette endpoint detection module (step 740) then searched left and right at the image row associated with said waist vertical image location and detects the left and right silhouette endpoints as white-black crossings of the binary images. Sub-pixel precision of endpoints is obtained from the grey-level image using sub-pixel edge/zero-crossing detection as well known in the art.

In a preferred embodiment, temporal vertical location filter (step 730) and temporal endpoints location filter (step 750) are applied to the sequence of values from preceding steps, in order to reduce noise and ignore outliers.

Temporal vertical location filter (step 730) is applied to the temporal sequence of vertical waist location, e.g., as indicated by {yWaist_0, yWaist_1, . . . } where _0, _1, etc. are image indices.

Temporal endpoints location filter (step 750) is applied to the temporal sequence of left waist location, e.g., { xLft_0, xLft_1, . . . } where _0, _1, etc. are image indices and similarly for the temporal sequence of right waist location.

The process repeats for each desired circumference value such as hips, chest, etc. To increase efficiency, as these body locations are known in advance, the process in FIG. 7 can be easily modified to obtain multiple temporal silhouette endpoint sequences during a single processing pass of the image sequence.

In the case that a full 3D model in the form of a cloud of points is required, the entire contour of the silhouette is traversed and converted into a list of edge points whose location is computed at sub-pixel precision as described hereinabove.

Figure 8A:
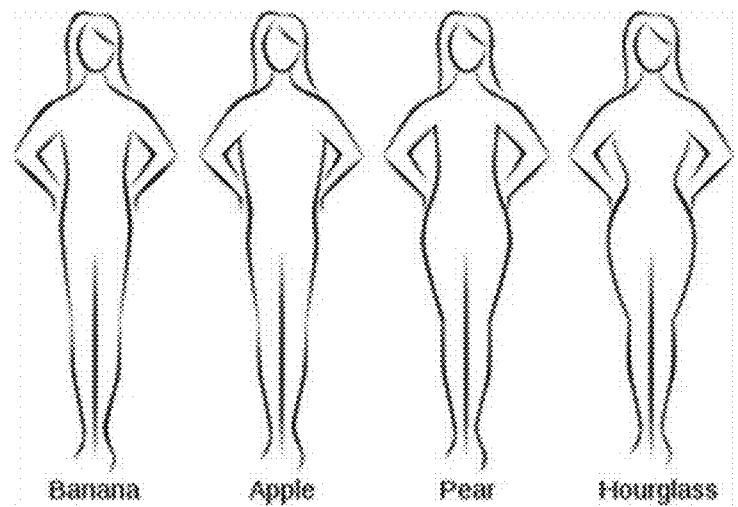
FIGS. 8A-8C schematically illustrate several cues for vertical waist location that can be executed by image analysis methods.
Figure 8C:
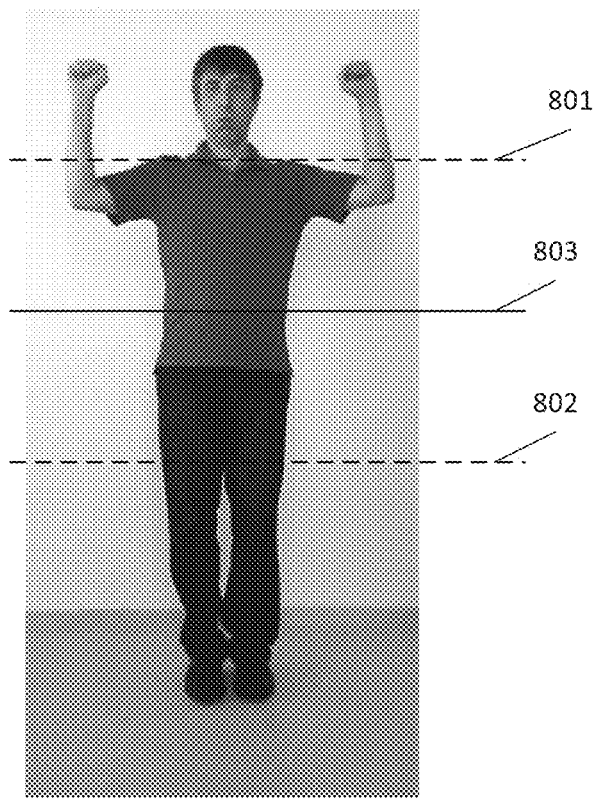
Figure 8B:
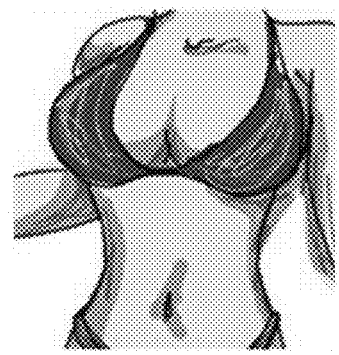

FIGS. 8A-8C schematically illustrate several cues for vertical waist location that can be executed by image analysis methods. For several body shapes (e.g., see FIG. 8A), the waist is defined as the narrowest point of the torso. A range of [y_min, y_max] image row coordinates is defined based on overall body silhouette size and a search for the smallest [x_left, x_right] interval is conducted. For better results, the subject's hand should be away from the body, either raised (e.g., as the user's position shown in FIG. 8C) or in 45 degrees, to avoid interference in the measurement. For more obese persons, the waist location might not be clear from the body width function. Therefore, another method for vertical waist detection can be used for detecting the visual feature points inside the user silhouette such as user's belly-button (as schematically illustrated in FIG. 8B). When none of the visual cues for waist location is stable enough, the system calculates the waist location from anthropometric data which for example provides the average waist height as a fraction of the user's height.

In addition to detecting 'natural' anatomical locations (e.g. waist, chest etc.) to the user's dimensions are extracted at nominal body locations, as requested for matching the user dimensions to specific garment dimensions. For example: for a certain garment the waist line is defined to be 45 cm from shoulder—we will locate the very same point along the body and measure the circumference at that very point.

FIG. 8C demonstrates another embodiment for vertical waist location, according to which the shoulder height and the crotch height are detected, based on silhouette analysis and the vertical waist location is proportionally defined between these two values. The shoulder height and the crotch height are indicated by dotted lines 801 and 802 respectively and the defined waist location in indicated by the line 803.

The image search for specific torso height lines like the waist line, the hips line and the chest line is further constrained by using anthropometric information. For example, the female waist point for 99% of all females lies between 0.578 and 0.652 of the female's height. Thus, knowing the subject gender and height as entered (e.g., during a registration process of a user to the system), together with the camera parameters allow us to compute the vertical image span of the waist area and conduct one or more of the waist detection processes described above, only in the that vertical image span. Similar anthropometric data facilitate the search for other body key-points such as the shoulders, neck, hand wrist, etc.

Figure 10A:
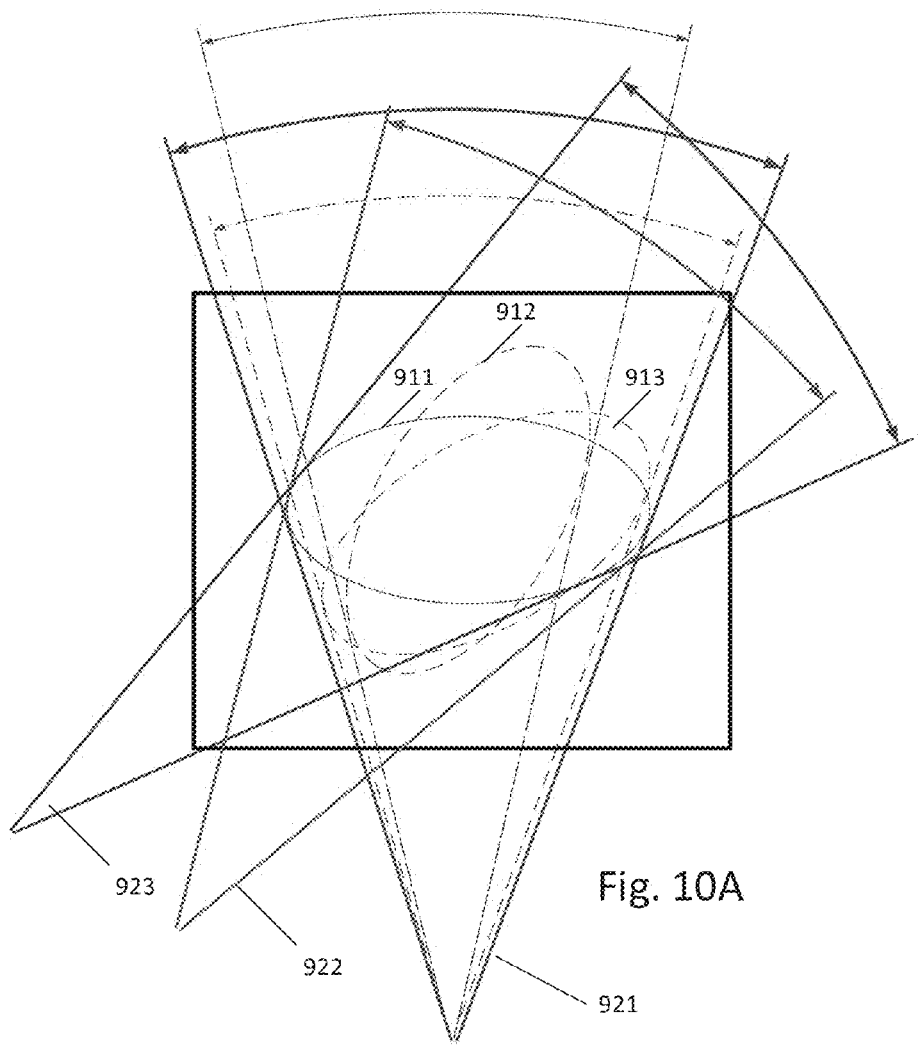
FIGS. 10A and 10B show how to obtain an accurate cross section shape from a sequence of images, according to an embodiment of the invention.
Figure 10B:
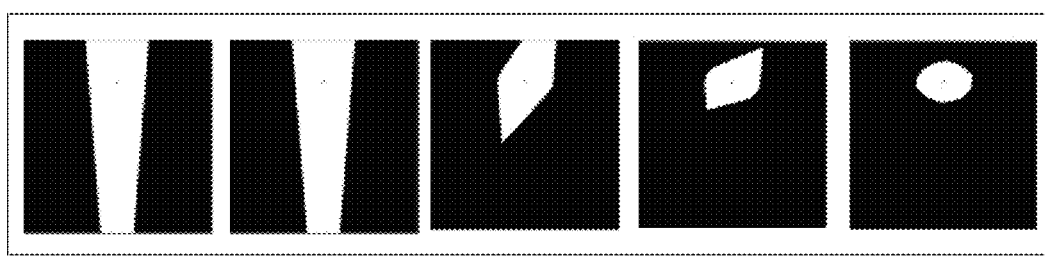
Figure 11:
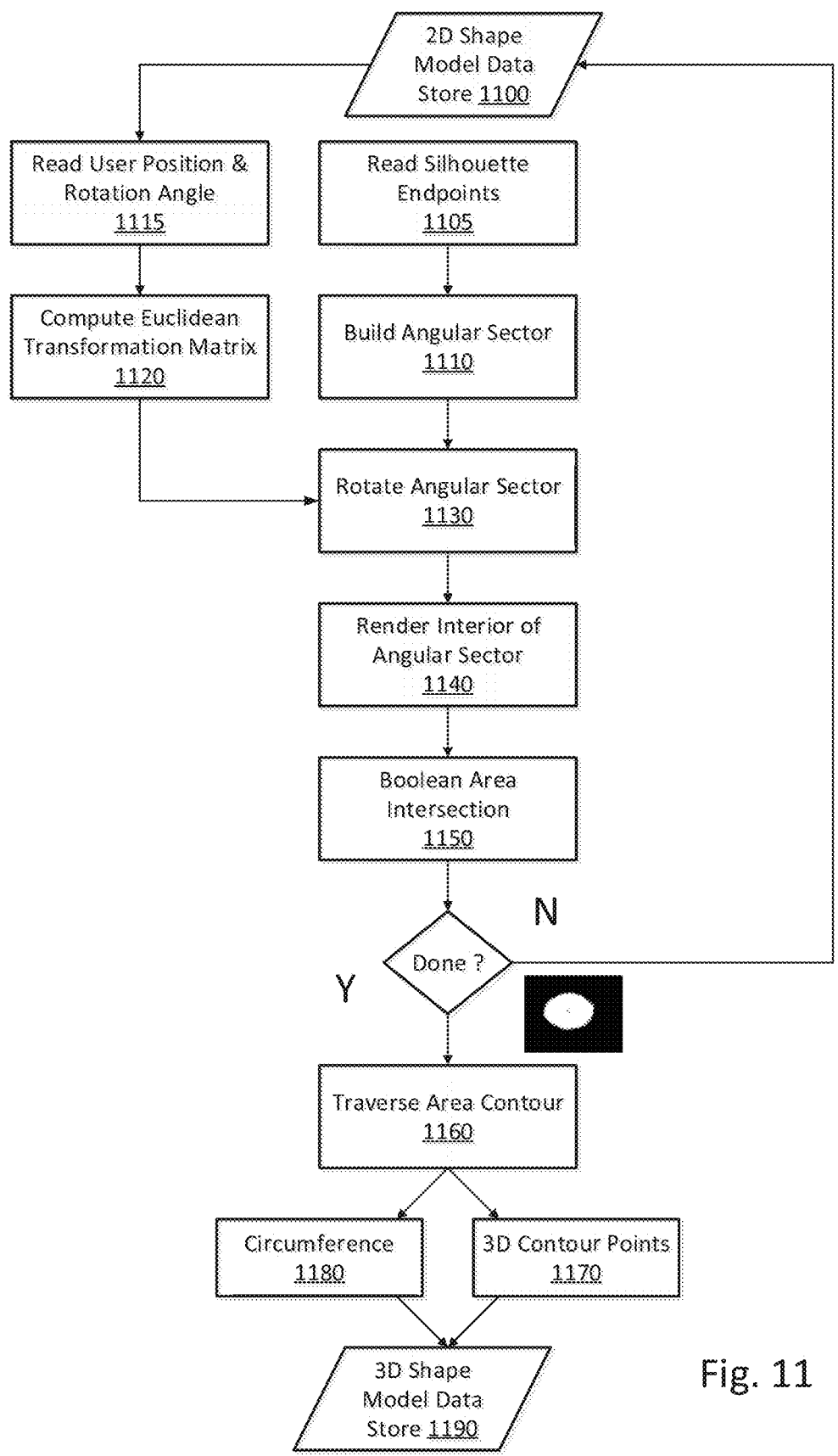
FIG. 11 describes the construction of 3D size metrics and shape data from 2D shape data.

FIGS. 9-11 depict the process of deriving circumference values from a sequence of 2D silhouettes, according to an embodiment of the present invention.

FIGS. 9A-9D schematically illustrate the principle of converting endpoints of a body silhouette 900 to a bounding angular sector. We will assume an orthographic (or parallel) projection model for the camera which can be justified for body parts at about the camera height or a distant camera (with respect to body dimensions). For other cases, correction factors can be experimentally obtained per elevation angle of the specific body part, with respect to the camera optical axis and used to correct the derived size measures/ derived 3D contour points.

Other correction factors relate to definition of certain body size measures. For example, the neck circumference is defined along a diagonal slice of the body 3D shape and a specific correction factor is applied for that measure.

Assuming a calibrated camera, each image point can be back-projected from the camera focal point (as indicated by numeral 906 in FIG. 9B), to describe a ray in space. The left and right endpoints (as indicated by numerals 901 and 902, respectively, in FIGS. 9B-9D) define an angular sector, which under the orthographic assumption/approximation lies in a plane parallel to the floor. The body cross section of the silhouette 900 at a specific height (such as waist, hips, etc.) is bounded by said angular sector, as indicated by numerals 903. Examples for other specific heights are indicated by numerals 904 and 905.

Camera calibration is known in prior art. Camera field of view and lens distortion data may be available from the manufacturer. For example, when using a smartphone such as an iPhone 4S by Apple Inc., the installed body measurement application according to the present invention may inquire the device, with a known Application Programming Interface (API) for the camera parameters.

Alternatively, intrinsic (field of view, distortion, optical center) and extrinsic (location and orientation) camera parameters can be obtained with a calibration pattern/object. Calibration software packages are also available as open source.

Ideally, the camera optical axis should be parallel to the floor surface. When this is not the case, the tilt can be detected and estimated from visual information such the location of the floor-wall intersection, or measured from the on-device sensors. Once the tilt information is available it is incorporated into the measurement equations to compensate for such tilt.

Figure 9A:
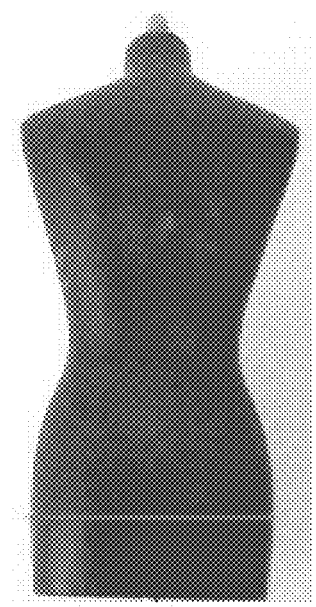
FIGS. 9A-9D illustrate the principle of converting silhouette endpoints to a bounding angular sector.
Figure 9B:
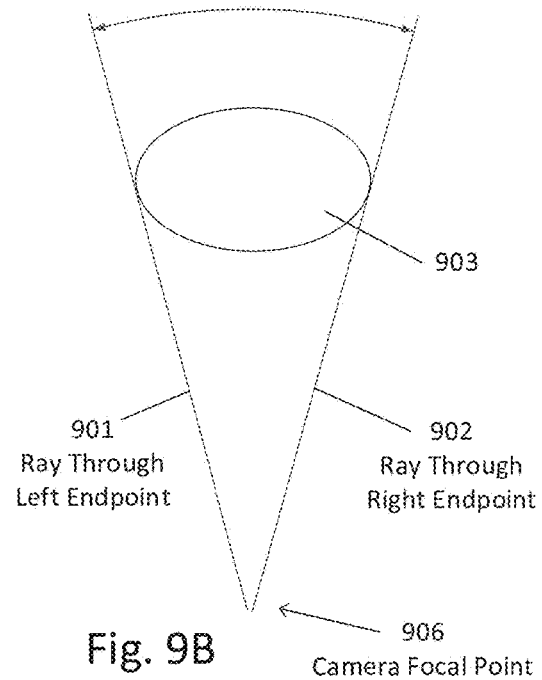
Figure 9C:
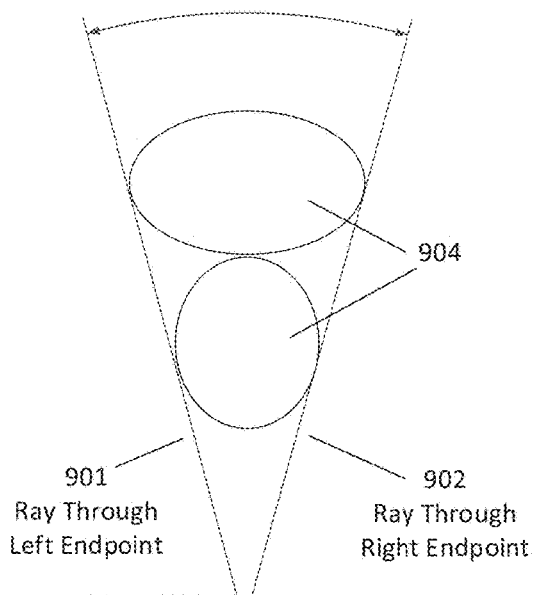
Figure 9D:
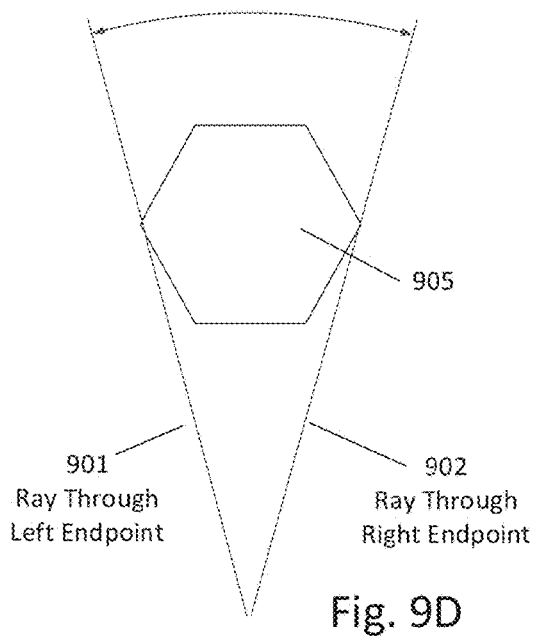

Of course, a single constraint (as obtained from a single 2D image of the body) tells us very little about the actual body size, since the actual body cross section in say waist level could be one of the shapes shown in FIG. 9B such as shape 902, 903, 904 or another shape. Note that another view (like a side view) reduces uncertainty and allows solving for the body circumference assuming an elliptical cross section. However, with real human bodies such an approximation is not accurate enough to provide the proper size recommendation or visualization.

FIGS. 10A and 10B show how to obtain an accurate cross section shape (and circumference) from a sequence of images of a freely rotating user. The figure depicts 3 poses as designated by elliptical contours that are indicated by numerals 911, 912 and 913. The elliptical contour 911 depicts a bounding area derived from the first reference pose. As the user rotates (counter-clockwise), its silhouette endpoint change and additional angular sectors, such as the elliptical contours 912 and 913 (dashed) are generated, for the rotated cross section.

Clearly to generate the cross section shape, the system must transform all angular sectors to the same frame of reference, chosen arbitrarily as the first position, for example. The Euclidean transformation is defined by the translation and rotation of the human body, with respect to the reference position. These motion parameters are obtained for the user behavior analysis module described hereinabove with respect to FIG. 3.

Back to FIG. 10A, after Euclidean transformation, the 3 constraint on body cross section shape are designated by the angular sectors 921, 922 and 923 (as indicated by the solid lines). The system now know more about said shape as it lies in the common area of all 3 sectors.

With multiple images (e.g., for a 10 second rotation the system may capture over 100 images), the system repeats the process of computing bounding angular sectors at the reference coordinate system, applying the respective Euclidean transformation to each sector and intersecting with the cumulative bounding shape. As more and more views of the body are added, the Boolean intersection of the sectors encloses the shape tighter and tighter, till the convex cross section is obtained. The Boolean intersection can be computed using the known technique of polygon intersection. This "object-space" approach as known in Computer Graphics has the advantage of computing the shape and its circumference at arbitrary precision.

Alternatively, an "image-based" approach according to the present invention renders the angular sectors one-by-one into a high-resolution bitmap which initially encompasses the entire measurement area (as indicated by the rectangle 930) and recursively applying Boolean intersection with the previous bitmap as shown in the series of exemplary black and white images in FIG. 10B.

FIG. 11 describes, in a flowchart form, the construction of 3D size metrics and shape data from 2D shape model data store (step 1100). For each 2D image analyzed by the 2DSA 140 (FIG. 1), silhouette endpoints coordinates are retrieved (step 1105) with user position and rotation angle (step 1115). The latter are used to compute 2D Euclidean transformation matrix (step 1120). Step 1110 builds a bounding angular sector in camera coordinates, which is shifted and rotated (by step 1130) using said matrix to the reference coordinate system. Step 1140 renders the interior of the angular sector, using convex polygon filling techniques as known in prior art. The rendering resolution (for example 5 pixels/cm) must be fine enough to avoid digitization errors. Step 1150 performs the Boolean intersection of the newly rendered angular sector with the shape coverage bitmap as accumulated so far.

When the full rotation sequence has been processed as described above, the shape of the cross section is available and its contour can be traversed, by step 1160. The contour may be represented by an array of contour points (step 1170) which can be converted into a 3D cloud of points, when accumulated with cross section of the figure at multiple heights. Alternatively the contour length is computed by step 1180 and serves as a circumference value for the waist. The obtained 3D shape model can be stored in a database (step 1190).

Figure 12:
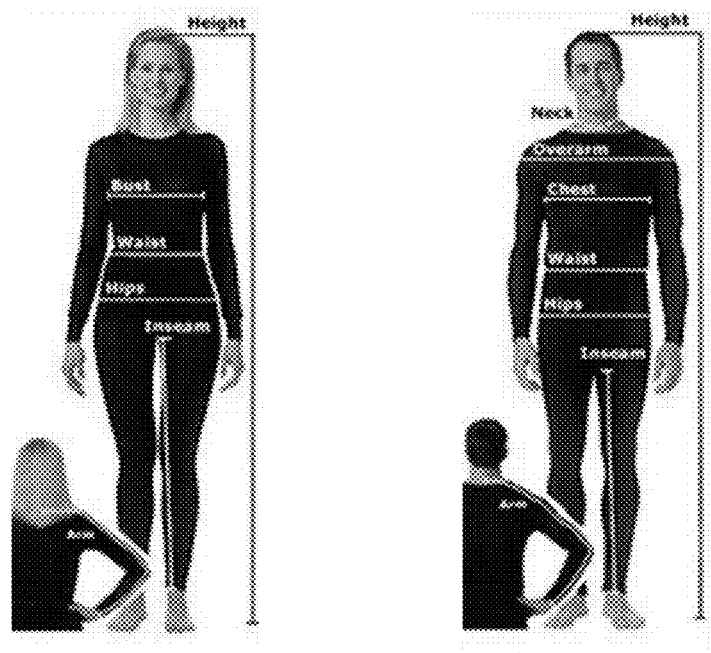
FIG. 12 depicts body torso size measures as usually required by the garment industry.

FIG. 12 depicts body size measures as usually required by the garment industry. Several key measures can be computed from a single user rotation in raised arms (so called "Cactus") position: Bust/Chest, Waist and Hips.

Other body size measures require the user to assume a different posture. For example, with the user's hands to the sides of his/her body, it is possible to get the overarm and neck circumference measures.

Additional body sizes are linear in nature. These include inseam, arm and height. Using calibration, such measures are extracted from a single frame, relying on user behavior analyzer 130 (FIG. 1) to select a fully frontal/backwards image for that measurement. Measuring legs is important for jeans and other tightly fitting garments. As legs suffer from mutual occlusion during a full body rotation, a modification to the method of the present invention would build the knee or ankle shape from those frames without occlusion. Since the leg cross section at the knee/angle is almost circular, visibility of the individual leg contour for 120° or rotational movement is sufficient for accurate estimation of the leg's circumference.

Figure 13A:
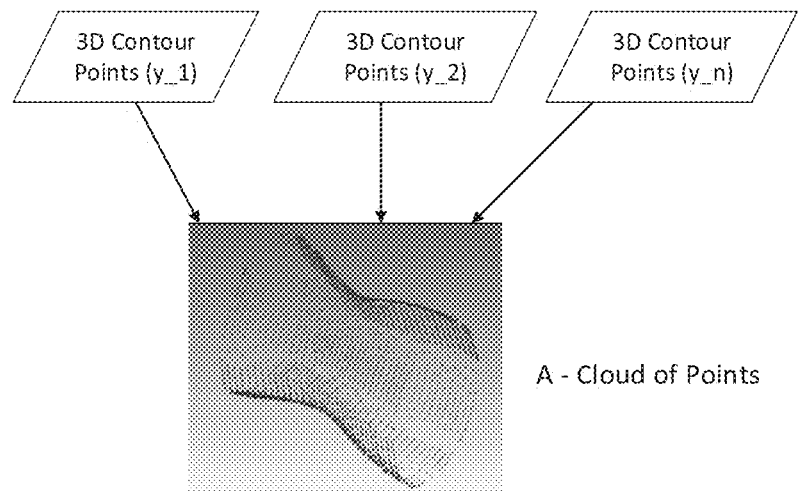
FIGS. 13A-13C schematically illustrate the construction of 3D model representations from generated 3D data.
Figure 13B:
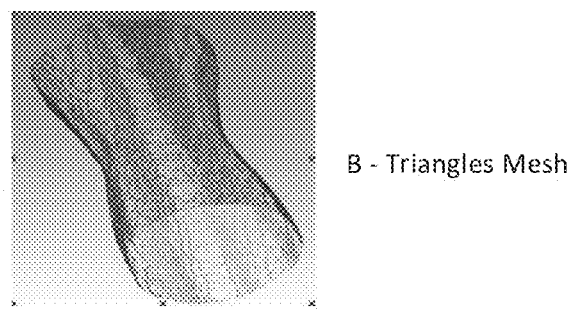
Figure 13C:
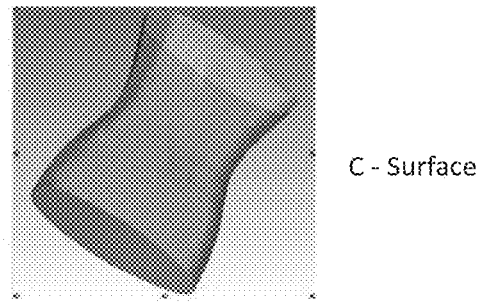

FIGS. 13A-13C schematically illustrate the construction of 3D model representations from generated 3D data according to an embodiment of the present invention. Repeating the process described with respect to FIG. 11 for a series of series of points, obtained from intersecting the silhouette contours from a sequence of image frames, at a sequence of elevation values, generates a cloud of points (FIG. 13A). Such a cloud of point can be converted to the format of full 3D body scanners. Furthermore, prior art as well as several commercially available software products, show how to convert the cloud of points to a series of polygons (see the illustrated triangles mesh in FIG. 13B) which serve as a surface model (see FIG. 13C), which may be better suited for virtual fitting room applications and for virtual clothing simulation.

Figure 14:
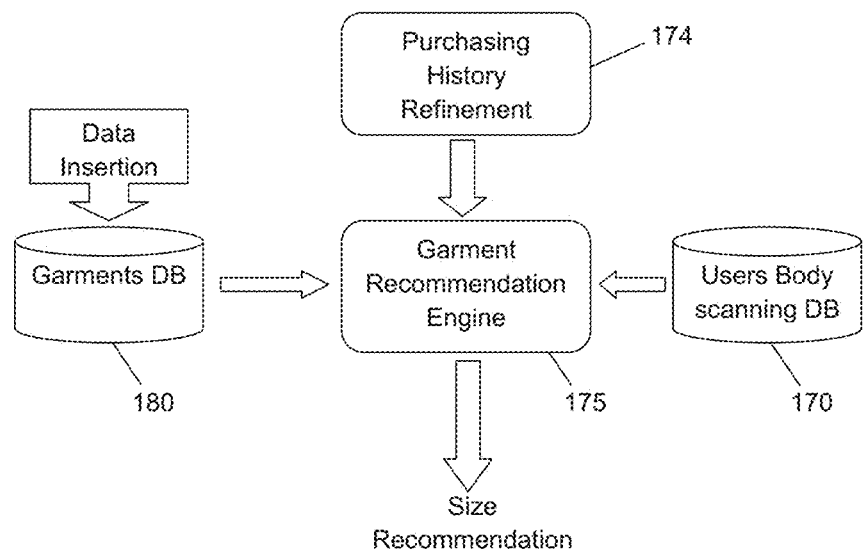
FIG. 14 schematically illustrates a Garment Recommendation Engine (GRE) according to an embodiment of the present invention.

FIG. 14 describes a Garment Recommendation Engine (GRE) 175 according to an embodiment of the present invention. The GRE 175 compares the user's body measurements (e.g. circumferences & lengths) to those of a selected garment and supplies recommendation regarding the best size fit.

Figure 15:
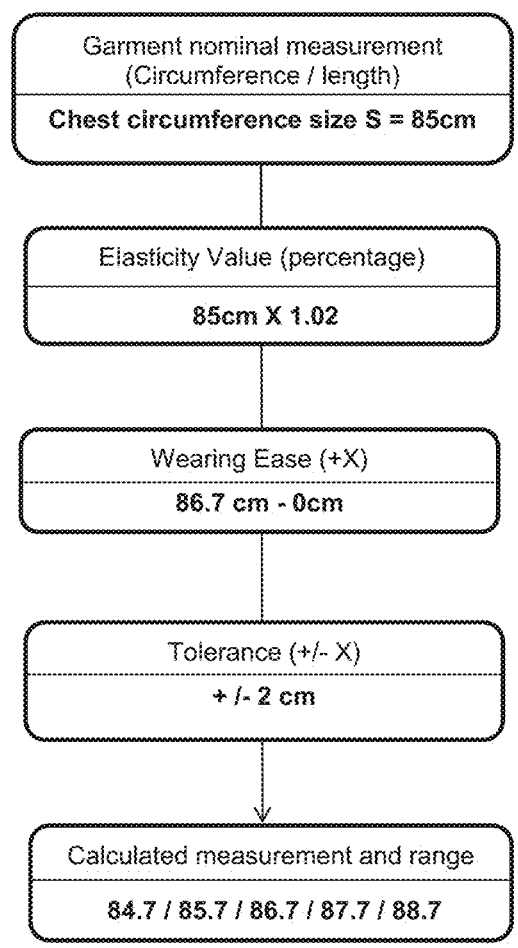
FIG. 15 schematically illustrates an exemplary size calculation flow in accordance with an embodiment of the present invention.

The GRE 175 receives the user's measurements from a user's body size measures database (e.g., such as the user shape and appearance database 170) and garments measurements from the Garments database 180. The garments data insertion to database 180 can be done either manually or automatically by a garment detection module. The GRE 175 may further receive purchasing history of the user as indicated by numeral 174. Each garment type (e.g. shirt, trousers, dress etc.) requires comparing a different set of circumferences and lengths, the number of measurements may also vary per retailer. The actual size of each garment which will be compared against the customer dimensions—depends also on parameters such as elasticity, wearing ease and tolerance. An exemplary size calculation flow is shown in FIG. 15 in accordance with an embodiment of the present invention.

Figure 16A:
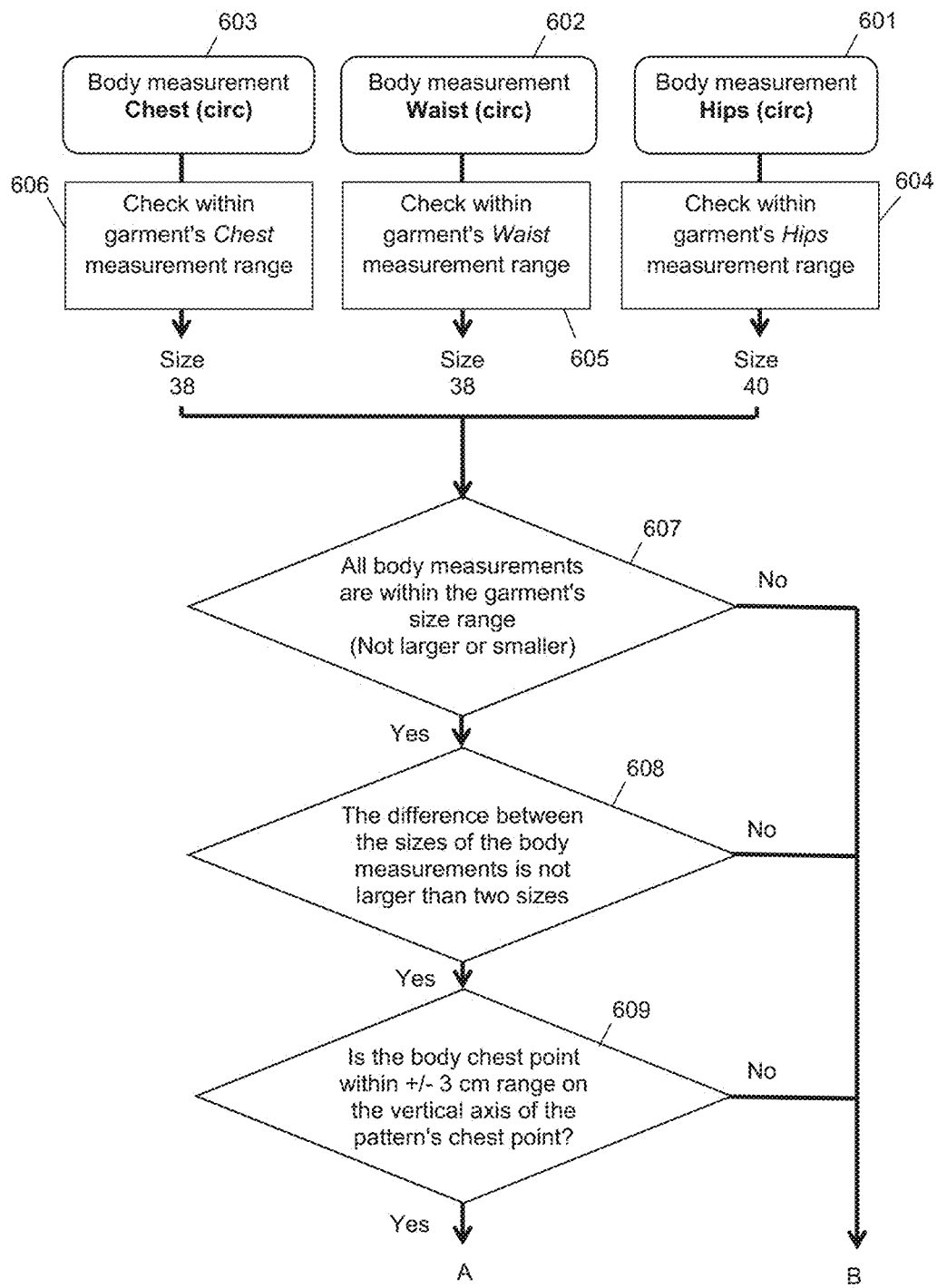
FIGS. 16A-16B schematically illustrate a process of issuing a size recommendation, according to an embodiment of the invention.
Figure 16:
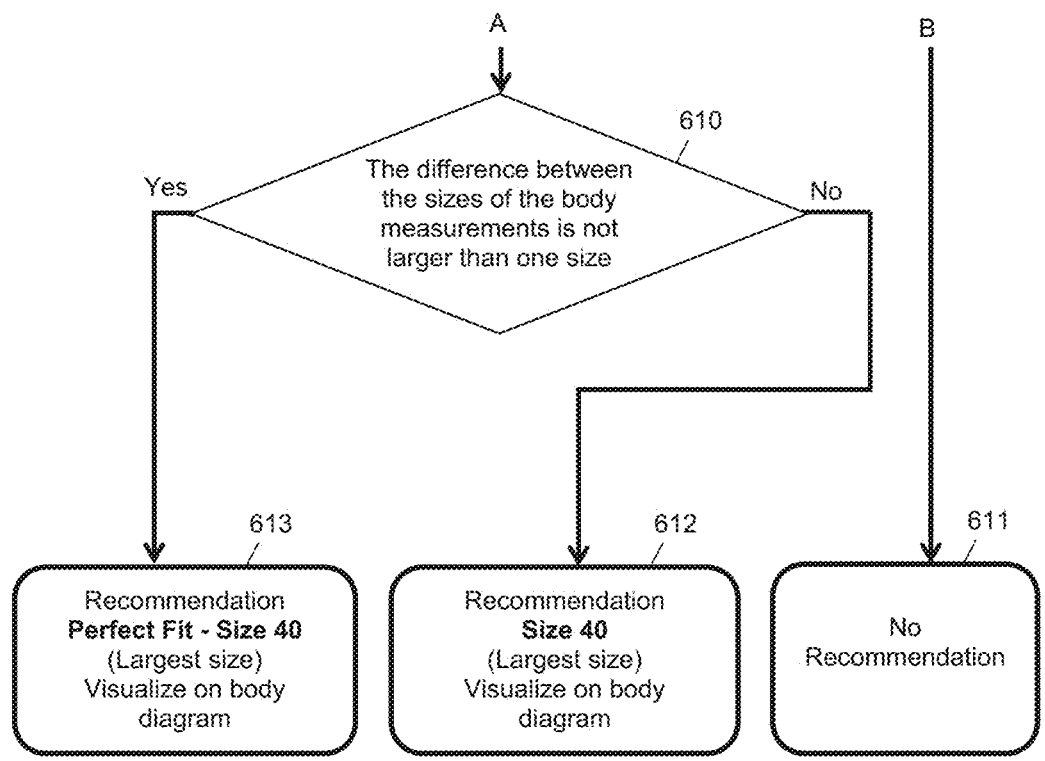
Figure 17:
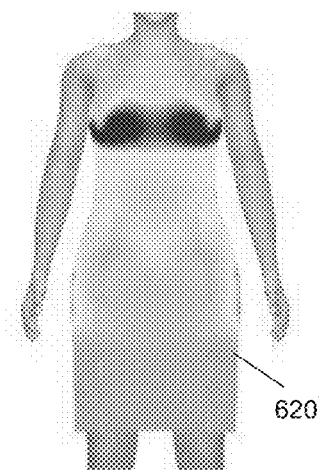
FIG. 17 schematically illustrates an example for a schematic heat map that depicts the way a garment fits the body of a user.

After the garment's measurements have been calculated and compared to the customer's body measurements, a size recommendation is issued, as for example, described in FIGS. 16A-16B accompanied by an illustration of the body fit presented by a heat map as indicated by numeral 620 in FIG. 17.

Referring now to FIGS. 16A-16B, for purpose of illustration only, the process of issuing a size recommendation may involve the following steps:

At first, the GRE 175 checks the body measurements (e.g., by checking a set of circumferences and lengths of a user's hips, waist and chest as indicated by numerals 601-606). In this example, the found circumferences sizes are chest size=38, waist size=38 and hips size=40.

At the next step (607), GRE 175 checks if all body measurements are within the garment's size range (not larger or smaller). If yes, then at the next step (608), it checks if the difference between the sizes of the body measurements is not larger than two sizes. If yes, then at the next step (609), it checks whether the body chest point within +/−3 cm range on the vertical axis of the pattern's chest point. Until this point, if the answer to any one of the checks of steps 607-609 is no, then no recommendation is obtained (step 611). If at step 609 the answer is yes, then at the nest step (610), the GRE 175 checks if the difference between the sizes of the body measurements is not larger than one size. If yes, (step 613), a recommendation for a perfect fit is provided (e.g., size 40—largest size), and the system visualize the garment on body diagram of the user (e.g., an avatar that mimics the user's appearance). If no, (step 612), a recommendation for the largest fit (e.g., size 40) is provided, but not necessarily a recommendation for a perfect fit as in step 613. For step 612, the system also visualizes the garment on body diagram of the user (e.g., an avatar that mimics the user's appearance).

It is important to mention that the above steps for issuing a size recommendation may refer only to a partial part of a much extensive logic that can include additional or other rules. For instance, the two size gap difference, described in the section above (see step 608), is just one exemplary rule from a large set of rules that can be utilized to enhance the efficiency of the size recommendation process.

According to an embodiment of the invention, the system can be configured to build an avatar from scanned user 2D shape data and/or from computed 3D shape data and optionally non-shape user characteristics (such as skin tone, eyes color, hair color). As aforementioned hereinabove, the avatar is used for visualization of the user during the scanning process (the idea is to present a figure that follows the user behavior—in order to enhance the experience and optionally create a sense of privacy by not showing the actual image captured by the camera).

The avatar can be further used for visualization of a selected garment for the user. Said visualization may be static or dynamic by animating the avatar with one of pre-defined/randomly generated movements. The avatar display can be modified (such as leaner that in reality) to enhance the user experience during scanning or to enhance the garment display during garment purchase stage.

The body measurement process according to the present invention can be used in diverse domains outside the fashion retail industry. One such domain is health. Obesity is becoming a significant health risk and therefore it is mandatory to provide means for monitoring obesity. A Body Mass Index (BMI) is a simple metric which is used extensively to measure obesity. However, BMI does not reflect the distribution of fat.

According to some embodiments of the invention, the body measurement process can be adapted for medical applications—scanning the user and analyzing the 3D shape data to produce certain health-related parameters/metrics such as obesity, fat distribution. In one embodiment, the scanning is conducted repeatedly (like monthly) and the user 3D shape data are compared with a reference scan or with one or more previous scans. The comparison process generates indications of significant changes of certain shape parameters.

As will be appreciated by the skilled person the arrangement described in the figures results in a system which is capable of capturing a sequence of 2D images of a human subject in motion with a single static 2D camera, extracting 2D shape or size-related descriptors from multiple such 2D images and integrating said descriptors into 3D size measures and/or elements of 3D shape.

According to an embodiment of the present invention, in order to get accurate properties of the garment, such as the length and width of the garment at several regions (e.g., neck region, belly region, sleeves, etc.), the angle of the camera with respect to a reference plane on which the garment is located should be considered. This is required in order to eliminate any distortion that may occur due to the non-parallel position (or non-optimal capturing angle) between the camera lens and the plane on which the garment is located.

Embodiments of the invention as were described hereinabove may be implemented as a computer process (method), a computing system, or as an article of manufacture, such as a computer program product or computer readable media. The computer program product may be a computer storage media readable by a computer system and encoding a computer program of instructions for executing a computer process.

Further, with respect to the example processes as described, not all the process states/steps need to be reached, nor do the states/steps have to be performed in the illustrated order. Further, certain process states that are illustrated as being serially performed can be performed in parallel.

Similarly, while certain examples may refer to a Personal Computer (PC) system or data device, other computer or electronic systems can be used as well, such as, without limitation, a tablet, a network-enabled personal digital assistant (PDA), a smart phone and so on.

The terms, "for example", "e.g.", "optionally", as used herein, are intended to be used to introduce non-limiting examples. While certain references are made to certain example system components or services, other components and services can be used as well and/or the example components can be combined into fewer components and/or divided into further components. Moreover, the example terminology as depicted and described herein, are intended to be illustrative and exemplary, and in no way limit the scope of the invention as claimed.

All the above description and examples have been given for the purpose of illustration and are not intended to limit the invention in any way. Many different mechanisms, methods of analysis, electronic and logical elements can be employed, all without exceeding the scope of the invention.

The invention claimed is:

1. A method for deriving accurate body size measures of a user from a sequence of 2D images, comprising:
    automatically guiding the user through a predefined sequence of body poses and motions, that include at least partial rotation, by providing a set of instructions, wherein said automatic guiding is based on real-time visual monitoring of the user and the surrounding scene;
    scanning the body of said user by obtaining a sequence of raw 2D images of said user as captured by at least one camera during said guided sequence of poses and motions;
    providing a user feedback and guidance module (UFGM) for interacting with the user during the scanning, including providing initial and further user guidance/assistance during the scanning;
    analyzing the behavior of said user to ensure that the user follows the provided instructions, by using a user behavior analyzer (UBA) module that tracks the position, pose/rotation and posture of said user before and during the guided sequence of poses and motions;

deterministically extracting and encoding 2D shape data descriptors from said sequence of images by using a 2D shape analyzer (2DSA); and integrating said 2D shape descriptors and data representing the user's position, pose and rotation into a 3D shape model, wherein said integration includes assigning rotation values to said sequence of images, wherein said values are either absolute values with respect to a full frontal position, or relative with respect to a reference image in said sequence.

2. A method according to claim 1, wherein integrating the 2D shape descriptors and data representing the user's position, pose and rotation into a 3D shape model includes deriving torso circumference values by intersecting convex areas computed by back projecting silhouette edge points according to user position and rotation associated with each silhouette image.

3. A method according to claim 2, wherein the torso circumference values are measure at one or more of: waist, hips and chest positions, and where the respective position is selected using at least one of: silhouette image analysis, extremum selection from a set of circumference values and anthropometric rations.

4. A method according to claim 1, wherein the initial user guidance/assistance includes at least one of: positioning the user with respect to the sensor field of view, positioning the user with respect to the background and background objects, advising the user to select a different location for the measurement process, advising the user to modify certain environmental elements in the scene, or advising the user one how to modify the device position and orientation.

5. A method according to claim 1, wherein the further user guidance/assistance includes at least one of: presenting a small audio-visual guide prior to the scanning process, before and during every step in the scanning sequence, presenting audio-visual instructions describing the posture/motion to be performed controlling the duration/pace of the posture motion by audible cues such as music/sound bites, monitoring the execution of the required postures and issuing corrective instructions, performing initial quality assessment of measurement metadata derived from current/prior postures/motions and guiding the user to repeat one or more postures/motions if so required.

6. A method according to claim 1, wherein presenting audio-visual instructions or issuing corrective instructions includes presenting a virtual guiding figure, positioned and scaled according to the user location.

7. A method according to claim 1, wherein the real-time visual monitoring of the user includes analyzing the scene/background as captured by the camera(s) by measuring dynamic and static image contents in said captured scene, thereby enabling to qualify the scene as a body measurement site, to suggest changes to the scene and to suggest optimal positioning for a location of the user in the scene.

8. A method according to claim 1, further comprising extracting and encoding visual non-shape descriptors of the user including face appearance descriptors of the user by a user appearance analyzer (UAA), wherein said non-shape descriptors represents attributes related to the appearance of said user and may include skin tone, hair color and style.

9. A method according to claim 1, further comprising estimating the distance from the user's image height and the user's physical height, as a single size value that either can be manually provided to the system via an input device, or the distance/location can be automatically extracted from the sequence of images.

10. A method according to claim 1, further comprising guiding the user to rotate at least a quarter of a circle and measuring the body rotation angle relative to a full frontal pose by tracking individual body parts that include at least left hand, right hand or top of head.

11. A method according to claim 1, further comprising detecting a body silhouette width evolution of the user as a key to body rotation, by tracking the evolution width sequence of binary images and estimating the rotation angles in-between using interpolation technique.

12. A method according to claim 1, wherein analyzing the behavior of the user further comprising verifying that user's image does not exceed the field of view of the camera.

13. A method according to claim 1, further comprising providing garment recommendation to the user by using a recommendation engine.

14. A system for deriving accurate body size measures of a user from a sequence of 2D images, comprising:
    a camera for scanning the body of said user by capturing a predetermined sequence of raw 2D images of said user;
    a user behavior analyzer (UBA) for analyzing the behavior of said user and to ensure that said user follows the provided instruction, by tracking the position, pose/rotation and posture of said user before and during the body scanning and matching them against stored posture/motion models stored in a Posture/Motion database;
    a user feedback and guidance module for interacting with the user during the scanning, including providing initial and further user guidance/assistance during the scanning;
    a 2D shape analyzer (2DSA) for deterministically extracting and encoding 2D shape data descriptors from said sequence of images; and
    a processing unit programmed for receiving said 2D shape descriptors as well as the user's position, pose and rotation data and integrating them into a 3D shape model, wherein said integration includes assigning rotation values to said sequence of images, wherein said values are either absolute values with respect to a full frontal position or relative, with respect to a reference image in said sequence.

15. A system according to claim 14, further comprising a user appearance analyzer (UAA) for extracting and encoding visual non-shape descriptors of the user.

16. A system according to claim 14, further comprising a user shape and appearance database for storing 3D size measurements of the user body together with the user appearance data.

17. A system according to claim 14, further comprising a garment database for storing garments related data.

18. A system according to claim 14, further comprising a garment recommendation engine (GRE) for providing garment recommendation to the user.

* * * * *